(12) United States Patent
Harichian et al.

(10) Patent No.: US 9,883,997 B2
(45) Date of Patent: *Feb. 6, 2018

(54) COSMETIC COMPOSITIONS WITH TRICYCLODECANE AMIDES

(71) Applicant: Conopco, Inc., Englewood Cliffs, NJ (US)

(72) Inventors: Bijan Harichian, Brookfield, CT (US); Teanoosh Moaddel, Watertown, CT (US); Ian Stuart Cloudsdale, Chapel Hill, NC (US); Van Au, Oxford, CT (US); Jianming Lee, Trumbull, CT (US); John Kenneth Dickson, Jr., Apex, NC (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/771,255

(22) PCT Filed: Mar. 10, 2014

(86) PCT No.: PCT/EP2014/054604
§ 371 (c)(1),
(2) Date: Aug. 28, 2015

(87) PCT Pub. No.: WO2014/139963
PCT Pub. Date: Sep. 18, 2014

(65) Prior Publication Data
US 2016/0008249 A1 Jan. 14, 2016

Related U.S. Application Data

(60) Provisional application No. 61/778,831, filed on Mar. 13, 2013.

(51) Int. Cl.
| | |
|---|---|
| *A61K 8/00* | (2006.01) |
| *A61K 8/49* | (2006.01) |
| *A61K 8/42* | (2006.01) |
| *A61Q 17/04* | (2006.01) |
| *C07D 215/08* | (2006.01) |
| *C07D 217/06* | (2006.01) |
| *C07C 233/58* | (2006.01) |
| *C07D 205/04* | (2006.01) |
| *C07D 207/06* | (2006.01) |
| *C07D 211/16* | (2006.01) |
| *C07D 211/60* | (2006.01) |
| *C07D 211/62* | (2006.01) |
| *C07D 211/66* | (2006.01) |
| *C07D 307/22* | (2006.01) |
| *A61Q 19/00* | (2006.01) |
| *A61K 8/34* | (2006.01) |
| *A61K 8/365* | (2006.01) |
| *A61K 8/368* | (2006.01) |
| *A61K 8/37* | (2006.01) |
| *A61K 8/63* | (2006.01) |

(52) U.S. Cl.
CPC ............ *A61K 8/4926* (2013.01); *A61K 8/347* (2013.01); *A61K 8/365* (2013.01); *A61K 8/368* (2013.01); *A61K 8/37* (2013.01); *A61K 8/42* (2013.01); *A61K 8/49* (2013.01); *A61K 8/4906* (2013.01); *A61K 8/4913* (2013.01); *A61K 8/4946* (2013.01); *A61K 8/4973* (2013.01); *A61K 8/63* (2013.01); *A61Q 17/04* (2013.01); *A61Q 19/00* (2013.01); *C07C 233/58* (2013.01); *C07D 205/04* (2013.01); *C07D 207/06* (2013.01); *C07D 211/16* (2013.01); *C07D 211/60* (2013.01); *C07D 211/62* (2013.01); *C07D 211/66* (2013.01); *C07D 215/08* (2013.01); *C07D 217/06* (2013.01); *C07D 307/22* (2013.01); *A61K 2800/10* (2013.01); *A61K 2800/49* (2013.01); *A61K 2800/52* (2013.01); *A61K 2800/591* (2013.01); *C07C 2603/74* (2017.05)

(58) Field of Classification Search
CPC ........ A61K 8/42; A61K 8/49; A61K 2800/10; A61Q 17/04; A61Q 19/00
See application file for complete search history.

(56) References Cited

U.S. PATENT DOCUMENTS

| | | | |
|---|---|---|---|
| 4,940,696 A | 7/1990 | Shroot et al. | |
| 4,956,481 A | 9/1990 | Gillaspey | |
| 4,985,403 A | 1/1991 | Narula | |
| 5,135,747 A | 8/1992 | Faryniarz | |

(Continued)

FOREIGN PATENT DOCUMENTS

| | | |
|---|---|---|
| CN | 102655845 | 9/2012 |
| DE | 10337579 | 4/2004 |

(Continued)

OTHER PUBLICATIONS

Search Report PCTEP2014054604 dated Jun. 11, 2014.
Search Report PCTEP2014054606 dated Jun. 11, 2014.
Written Opinion 1 in PCTEP2014054604 dated Jun. 11, 2014.
Written Opinion 1 in PCTEP2014054606 dated Jun. 11, 2014.
Akhrem et al., "Alkanes and cycloalkanes in the one-pot synthesis of amides", Mendeleev Communications, 2007, vol. 17, pp. 279-280.
Akhrem et al., "The first one-pot amidation of alkanes and cycloalkanes", Tetrahedron Letters, Jan. 10, 2008, vol. 49, pp. 1399-1404.
Kasemura et al., "Miticidal Activity of Monoterpenyl Carboxypyrrolidinamides and Piperidinamides", Journal of Oleo Science, 2003, vol. 52, No. 1, pp. 41-46.
Kontonassios et al., "3-(Dialkylamino)methyladamantane-1-carboxylic Acids", Notes, Apr. 29, 1968, vol. 12, pp. 170-172.
Egan et al., Raoult's law and vapor pressure measurement, Journal of Chemical Education, May 1, 1976, vol. 53, No. 5, p. 303.
Schafer et al., "Facile synthesis of Sterically Hindered and Electron-Deficient Secondary Amides from Isocyanates", Angew. Chem. Int. Edition, Sep. 3, 2012, vol. 51, No. 36, pp. 9173-9175; XP055120011.

(Continued)

*Primary Examiner* — Robert A Wax
*Assistant Examiner* — Olga V Tcherkasskaya
(74) *Attorney, Agent, or Firm* — Ellen Plotkin

(57) ABSTRACT

The invention is directed to a cosmetic composition and the precursor thereof. The composition has solid agent and liquid agent, both of which are cosmetic benefit ingredients. The solubility of solid agents in liquid agents in the inventive compositions is enhanced in the presence of a tricyclodecane amide.

13 Claims, 1 Drawing Sheet

(56) References Cited

U.S. PATENT DOCUMENTS

| | | | |
|---|---|---|---|
| 5,212,203 A * | 5/1993 | Shroot | C07D 295/192 514/617 |
| 5,212,303 A | 5/1993 | Shroot | |
| 5,833,999 A | 11/1998 | Trinh | |
| 5,849,310 A | 12/1998 | Trinh | |
| 6,086,903 A | 7/2000 | Trinh | |
| 6,100,233 A | 8/2000 | Sivik | |
| 6,399,045 B1 | 6/2002 | Morgan | |
| 6,576,228 B1 | 6/2003 | Crookham | |
| 7,282,522 B2 | 10/2007 | Rho et al. | |
| 8,053,431 B2 | 11/2011 | Kilburn | |
| 8,173,108 B2 * | 5/2012 | Misso | A61K 8/042 424/59 |
| 2003/0003119 A1 * | 1/2003 | Bekele | A61K 8/33 424/401 |
| 2004/0228814 A1 | 11/2004 | Candau | |
| 2006/0024337 A1 | 2/2006 | Simonnet | |
| 2006/0057083 A1 | 3/2006 | Mathonneau | |
| 2006/0062746 A1 | 3/2006 | Brillouet | |
| 2006/0166856 A1 | 7/2006 | Petrat | |
| 2011/0104082 A1 | 5/2011 | Polonka | |
| 2011/0104087 A1 | 5/2011 | Polonka | |
| 2012/0004206 A1 | 1/2012 | Pliushchev | |

FOREIGN PATENT DOCUMENTS

| | | | |
|---|---|---|---|
| DE | 10337579 A | 4/2004 | |
| DE | 10337579 | 4/2014 | |
| EP | 0199636 | 2/1989 | |
| EP | 1010685 | 6/2000 | |
| ES | 2296463 | 4/2008 | |
| ES | 2296463 | 2/2009 | |
| WO | WO9918919 | 6/1999 | |
| WO | WO03075878 | 9/2003 | |
| WO | WO 03075878 A2 * | 9/2003 | A61K 8/35 |
| WO | WO2004089415 | 10/2004 | |
| WO | WO2004089416 A2 | 10/2004 | |
| WO | WO2004089470 A3 | 10/2004 | |
| WO | WO2005019162 | 3/2005 | |
| WO | WO 2005019162 A1 * | 3/2005 | A61K 8/40 |
| WO | WO2006119283 A2 | 11/2006 | |
| WO | WO2008054144 | 5/2008 | |
| WO | WO 2008054144 A1 * | 5/2008 | A61K 8/42 |
| WO | WO2011054704 | 6/2011 | |

OTHER PUBLICATIONS

Schuster et al., "The Discovery of New 11B-Hydroxysteroid Dehydrogenase Type 1 Inhibitors by Common Feature Pharmacophore Modeling and Virtual Screening", Journal of Medical Chem, 2006, vol. 49, pp. 3454-3466, 49.

Search Report in PCTEP2014054587 dated Oct. 14, 2014.

Terao et al., "11B-Hydroxysteroid Dehydrogenase-1 Is a Novel Regulator of Skin Homeostasis and a Candidate Target for Promoting Tissue Repair", PLos One, Sep 2011, vol. 6 Iss 9, pp. 1-11.

Tiganescu et al., "Localization, Age-and Site-Dependent Expression, and Regulation of 11B-Hydroxysteroid Dehydrogenase Type 1 in Skin", Journal of Invesitgative Dermatology, 2011, vol. 131, pp. 30-36.

Hermanowski-Vosatka et al., "11B-HSD1 inhibition ameliorates metabolic syndrome and prevents progression of atherosclerosis in mice", Journal of Experimental Medicine, Aug. 15, 2005, vol. 202, No. 4, pp. 517-527, vol. 202 No. 4.

Webster et al., "Discovery and biological evaluation of adamantyl amide 11B-HSD1 inhibitors", Bioorganic & Medicinal Chemistry Letters, 2007, vol. 17, pp. 2838-2843, 17.

Written Opinion 2 in PCTEP2014054604 dated Feb. 10, 2015.

Written Opinion 2 in PCTEP2014054606 dated Feb. 10, 2015.

Written Opinion in PCTEP2014054587 dated Oct. 14, 2014.

He Tielin et al., Handbook of Water Treatment Chemicals 1st Ed 2000 pp. 116-118 With Translation, Chemical Industry Press.

Written Opinion in EP14708586, dated Aug. 2, 2017.

* cited by examiner

COSMETIC COMPOSITIONS WITH TRICYCLODECANE AMIDES

FIELD OF THE INVENTION

The present invention is directed to a cosmetic composition and method for stabilizing the composition with a tricyclodecane amide. The tricyclodecane amide unexpectedly enhances the solubility of solid agents within liquid agents of the composition and results in a superior cosmetic composition suitable for topical use by consumers.

BACKGROUND OF THE INVENTION

A large number of solid agents used in cosmetic compositions, for example, often have low solubilities in solvents or liquid agents, and thus a tendency to recrystallize rapidly within the compositions. Recrystallization of solid cosmetic agents, not only negatively impacts the performance of the cosmetic composition but also can result in a grainy composition having inferior sensory attributes.

With sunscreens, for example, in order to achieve good protection, excessively large proportions of oily solvents are often needed to enhance solubility of the sunscreen. This approach, however, invariably yields a final cosmetic composition that delivers an oily or greasy feel that is not typically enjoyed by consumers.

Another technique employed to prevent solid agent recrystallization in compositions is encapsulation. Encapsulation, nevertheless, can be expensive and prevents solubilization of solid agent within a composition (like a cosmetic composition). As a result of this, it is often observed that less agent (e.g., active) is delivered through skin when the same is encapsulated and applied topically.

There is an increasing interest to develop cosmetic compositions for topical application that minimize recrystallization in the absence of encapsulation. Moreover, there is an increasing interest to enhance solubility of solid agents within compositions so that a maximum amount of such agents may be delivered topically to consumers from cosmetic compositions. This invention, therefore, is directed to stabilized cosmetic compositions that comprise a tricyclodecane amide. The tricyclodecane amide unexpectedly enhances solubility of solid agents in liquid agents within the compositions. The enhancement of solid agent solubility is surprisingly achieved while simultaneously delivering compositions that yield excellent sensory benefits upon topical application. Although not wishing to be bound by this theory, it is believed that tricyclodecane amides have a unique cage structure, which renders them small and bulky, therefore allowing them to disturb the ordered packing and formation or growth of crystals. Also as part of the present invention it has been discovered that tricyclodecane amides themselves have cosmetic benefits, such as sebum suppression and boosting UV-A, UV-B, and SPF performance of common sunscreen agents.

Additional Information

Efforts have been disclosed for increasing the solubility of benefit agents within a cosmetic composition. In United States Patent Application No. 2006/0024337 A1, a process is described for dissolving lipophilic compounds with amphiphilic block copolymers in cosmetic compositions. Other efforts have been described for enhancing benefit agent deposition within personal wash compositions. In U.S. Pat. No. 6,576,228 B1, personal wash compositions with water-soluble compounds for providing enhanced SPF are described. Still other efforts have been disclosed for enhancing benefit agent deposition. In U.S. Pat. No. 6,399,045 B1, liquid personal wash compositions with benefit agent and cationic polymers are described.

Tricyclodecane derivatives, and in some cases tricyclodecane amides, have been described. See for instance Kilburn et al., U.S. Pat. No. 8,053,431B2; WO2004/089415A2 (Novo Nordisk NS); WO2004/089416A2 (Novo Nordisk NS); Narula et al., U.S. Pat. No. 4,985,403; Mathonneau, US 2006057083; WO06/119283 (Hunton & Williams LLP); WO08/054144 (Amorepacific Corporation).

SUMMARY OF THE INVENTION

The present invention includes a cosmetic composition precursor comprising:
 a) a tricyclodecane amide;
 b) a solid agent;
 c) a liquid agent;
 d) wherein both the solid agent and the liquid agent is a cosmetic benefit agent; and
 e) wherein solid agent to liquid agent weight ratio is in the range from about 0.001 to about 1.

The present invention also includes a cosmetic composition comprising the cosmetic composition precursor.

The present invention also includes a method of delivering a solid cosmetic agent topically to the skin of a consumer with the composition of this invention.

"Solid agent", as used herein, means an agent (e.g., mixture, compound) that is a solid at room temperature (melting point above 20° C.), such solid agent having a partition coefficient (Log $P_{o/w}$) from about −5 to about 15.

"Cosmetic benefit agent", as used herein, means a component or benefit agent that improves a characteristic of teeth, a skin or hair characteristic and/or benefits teeth, skin or hair wherein the same can be, and preferably, is an active in a cosmetic composition, and most preferably, in a topical cosmetic composition classified as a dentifrice, mouthwash, cream (including vanishing), lotion, balm, deodorant, gel, make-up composition, body wash, shampoo or conditioner.

"Liquid agent," as used herein, means an agent (e.g., mixture, compound) that is a liquid at room temperature (melting point below 20° C.), such liquid agent having a partition coefficient (Log $P_{o/w}$) from about −0.75 to about 15.

The octanol-water partition coefficient for solid and liquid agents can be obtained from a variety of published sources such as CRC Handbook of Physics and Chemistry or through the use of on-line software such as ChemSpider. The values reported for Log P of solid and liquid agents in this invention were taken from the on-line ChemSpider source.

Both the solid agent and the liquid agent is a cosmetic benefit agent as described herein. Solid agent and liquid agent are not meant to include agents or ingredients used solely to produce a cosmetic carrier or chassis such as water, polymeric thickeners such as polyacrylates, Aristoflex AVC, silicon containing polymers, emulsifiers, opacifiers, microspheres such as those supplied by Kobo Products Inc. examples include polymethylmethacrylate e.g. BPA-500, ethylene/methacrylate copolymers e.g. EA-209, Nylon series such as Nylon-6 e.g. TR-1, Polyethylene e.g. CL2080, polymethylsilsesquioxane e.g. Tospearl series, Silica series e.g. MSS-500, cellulose beads series e.g. Cellulo Beads D-5, others also excluded are starch and modified starch such as the Dry-Flo series from AkzoNobel, pigments or colorants, pH modifiers or buffers and chelators.

"Cosmetic composition", as used herein, means end use cosmetic composition, the same preferably being an end use composition applied topically to the skin and/or hair of humans.

"Cosmetic composition precursor", as used herein, means an additive suitable for use as an ingredient mixture added to a cosmetic composition that is end use for consumer application. Such a composition precursor typically makes up from about 0.001 to about 90%, and preferably, from about 0.5 to about 75%, and most preferably, from about 1 to about 50% by weight of the composition, based on total weight of the composition and including all ranges subsumed therein.

"Skin", as used herein, is meant to include skin on the face, neck, chest, back, arms (including underarms), hands, legs, buttocks and scalp. In an especially preferred embodiment, the cosmetic composition of this invention is a leave-on composition for topical application to skin.

"Comprising", as used herein, is meant to include consisting essentially of and consisting of. Therefore, and by way of illustration, comprising tricyclodecaneamide, solid agent and liquid agent provides support for consisting essentially of and consisting of the same.

All ranges identified herein are meant to include all ranges subsumed therein if, for example, reference to the same is not explicitly made. It should be noted that in specifying any range of concentration or amount, any particular upper concentration can be associated with any particular lower concentration or amount.

Except in the operating and comparative examples, or where otherwise explicitly indicated, all numbers in this description indicating amounts of material ought to be understood as modified by the word "about".

DETAILED DESCRIPTION OF THE PREFERRED EMBODIMENT

Tricyclodecane Amide

Figure 1:
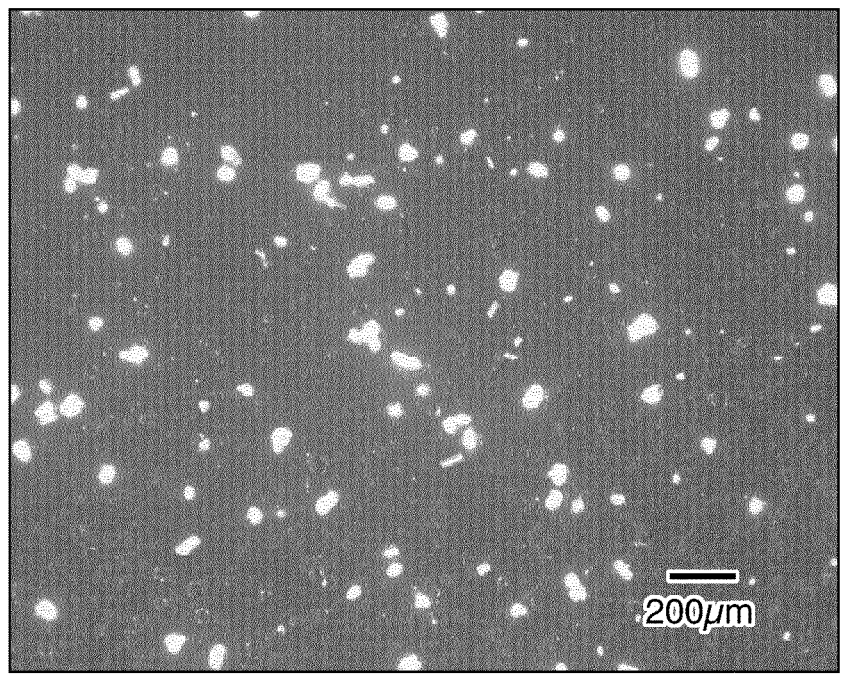
FIG. 1 and FIG. 2 are microphotographs of the Sample 30 (FIG. 1) and Comparative Sample A (FIG. 2), made 72 hours after cooling to room temperature using Leitz Pol S optional microscope fitted with cross-polarizers at magnitude 40×.

There generally is no limitation with respect to the tricyclodecane amide that may be used in this invention other than that the same is suitable for use in compositions used by consumers. Often, however, the tricyclodecane amide suitable for use in this invention is represented by at least one compound having Formula I or Formula II. Tricyclodecane amides of Formula I are preferred.

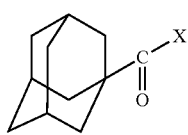

Formula I

Where X is selected from:

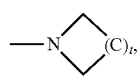

Xa

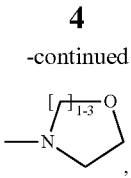

Xb

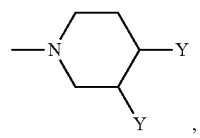

Xc

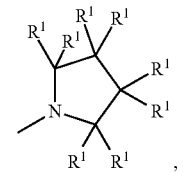

Xd

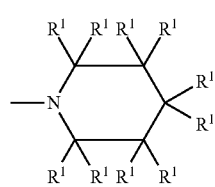

Xe

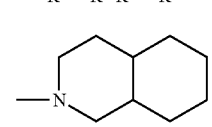

Xf

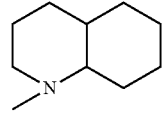

Xg

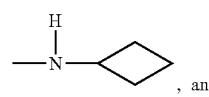

Xh

, and

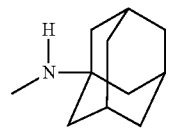

Xi further wherein t is an integer from 1 to 8; Y is

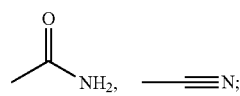

hydrogen, or a halogen where each $R^1$ is independently a hydrogen or a $C_{1\ to\ 4}$ alkyl.

Preferably, X is selected from groups Xd, Xe, Xf, Xg and, and more preferably Xd and Xe, ideally X is selected from groups Xe and Xd, wherein $R^1$ is hydrogen on all but one carbon and is mono- or di-substituted on that single carbon with methyl or ethyl groups.

Preferred Formula I compounds, wherein X is group Xa, Xb, Xc, Xd, Xe, Xf, Xg, Xh, Xi are:

Methanone, (morphonyl)tricyclo[3.3.1.1$^{3,7}$]dec-1-yl-(C1)
Methanone, (piperidinyl)tricyclo[3.3.1.1$^{3,7}$]dec-1-yl-(C2)
Methanone, (pyrrolidinyl)tricyclo[3.3.1.1$^{3,7}$]dec-1-yl-(C3)
Methanone, (azetidinyl)tricyclo[3.3.1.1$^{3,7}$]dec-1-yl-(C4)
Methanone, (hexahydroazepinyl)tricyclo[3.3.1.1$^{3,7}$]dec-1-yl-(C5)
Methanone, (4-cyano-piperidinyl)tricyclo[3.3.1.1$^{3,7}$]dec-1-yl-(C6)
Methanone, (4-amido-piperidinyl)tricyclo[3.3.1.1$^{3,7}$]dec-1-yl-(C7)
Methanone, (Tricyclo[3.3.1.1$^{3,7}$]decanyl)-N-tricyclo[3.3.1.1$^{3,7}$]dec-1-yl-(C8)
Methanone, (decahydroisoquinolinyl)tricyclo[3.3.1.1$^{3,7}$]dec-1-yl-(C9)
Methanone, (decahydroquinolinyl)tricyclo[3.3.1.1$^{3,7}$]dec-1-yl-(010)
Methanone, (3,3-dimethyl-1-piperidinyl)tricyclo[3.3.1.1$^{3,7}$]dec-1-yl-(C11)
Methanone, (2-methyl-1-piperidinyl)tricyclo[3.3.1.1$^{3,7}$]dec-1-yl-(C12)
Methanone, (4-methyl-1-piperidinyl)tricyclo[3.3.1.1$^{3,7}$]dec-1-yl-(C13)
Methanone, (3-methyl-1-piperidinyl)tricyclo[3.3.1.1$^{3,7}$]dec-1-yl-(C14)
Methanone, (3,5-dimethyl-1-piperidinyl)tricyclo[3.3.1.1$^{3,7}$]dec-1-yl-(C15)
Methanone, (4-methyl-4-ethy-piperidinyl)tricyclo[3.3.1.1$^{3,7}$]dec-1-yl-(C16)
Methanone, (3,3-diethyl-1-pyrrolidinyl)tricyclo[3.3.1.1$^{3,7}$]dec-1-yl-(C17)

-continued

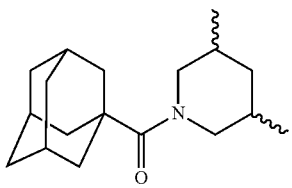
(C15)

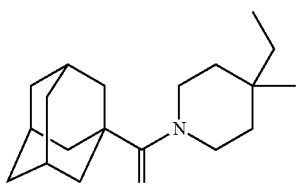
(C16)

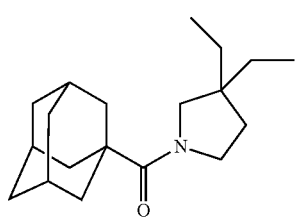
(C17)

More preferred compounds are compounds C9 through C17, and most preferred compounds are C11 through C17.

Tricyclodecane amides of Formula II have the following general structure:

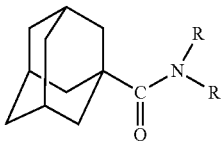

Formula II wherein each R is independently hydrogen, methyl, ethyl or a $C_3$ to $C_{18}$, preferably $C_3$ to $C_{10}$, linear or branched alkyl, cycloalkyl or cycloheteroalkyl group, with the proviso that both R groups are not simultaneously hydrogen:

Methanone, (N,N-diisopropyl) tricyclo[3.3.1.1$^{3,7}$]dec-1-yl-(C18)

Methanone, (3,3-dimethylbutylaminyl) tricyclo[3.3.1.1$^{3,7}$]dec-1-yl-(C19)

Methanone, (2,2-dimethylpropylaminyl) tricyclo[3.3.1.1$^{3,7}$]dec-1-yl-(C20)

Methanone, (1,1-dimethyl-3,3-dimethylbutylaminyl) tricyclo[3.3.1.1$^{3,7}$]dec-1-yl-(C21)

Methanone, (1,3-dimethyl-butylaminyl) tricyclo[3.3.1.1$^{3,7}$]dec-1-yl-(C22)

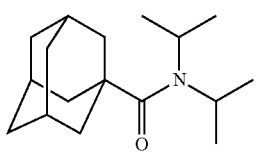
(C18)

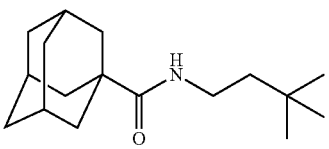
(C19)

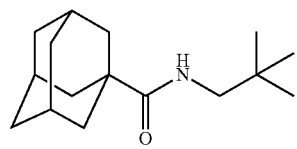
(C20)

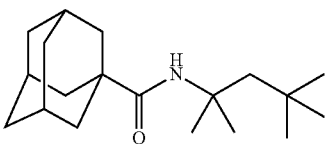
(C21)

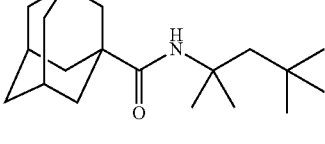
(C22)

Wherein compounds C19, C20, C21 and C22 are more preferred, and compounds C21 and C22 most preferred.

Tricyclodecane amide may make up from 0.0001 to 20%, and preferably, from 0.001% to 10%, and most preferably, from 0.01% to 5% by weight of the composition, including all ranges subsumed therein. With regards to the composition precursor, it is desired for the weight percent of tricyclodecane amide to be the same as defined in the composition to at least about 15% higher, based on total weight of the composition precursor.

Other tricyclodecane amides and other tricyclodecane derivatives may be included in the inventive composition, in addition to the tricyclodecane amides described herein.

Carrier/Chassis Ingredients

Carriers are not solid or liquid agents within the meaning of this invention. Cosmetically acceptable components for carriers can include water, silicone oils, emulsifiers and polymeric thickeners. Amounts of these materials may range from 0.1 to 99%, and preferably, from 0.1 to 80%, and most preferably, from 1 to 50% by weight of the composition, including all ranges subsumed therein.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from 3 to 9, and preferably, from 4 to 5 silicon atoms.

Linear volatile silicone materials generally have viscosities of less than 5 centistokes at 25° C. while cyclic materials typically have viscosities of less than 10 centistokes.

Nonvolatile silicone oils useful as carrier material include polyalkyl siloxanes, polyalkylaryl siloxanes and polyether siloxane copolymers. The essentially non-volatile polyalkyl siloxanes useful herein include, for example, polydimethylsiloxanes (like dimethicone) with viscosities of from 5 to 100,000 centistokes at 25° C. Silicone oils, (especially, Dimethicone 35 to 75 centistokes) suitable for use, are often made commercially available from Dow Corning are preferred.

Amounts of silicones, when used, may range from 0.001% to 80%, and preferably from 0.01% to 50%, and most preferably from 0.01% to 30% by weight of the composition, including all ranges subsumed therein.

The emulsifier may be selected from the group consisting of anionic, nonionic, cationic, polymeric and amphoteric actives. Particularly preferred nonionic actives are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) are also suitable nonionic emulsifiers. Preferred anionic emulsifiers include alkyl ether sulfate and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, alkylethercarboxylates and combinations thereof.

Cationic emulsifiers that may be used include, for example, palmitamidopropyltrimonium chloride, distearyldimonium chloride and mixtures thereof. Useful amphoteric emulsifiers include cocoamidopropyl betaine, $C_{12}$-$C_{20}$ trialkyl betaines, sodium lauroamphoacetate, and sodium laurodiamphoacetate or a mixture thereof.

Other generally preferred emulsifiers include glyceryl stearate, glycol stearate, stearamide AMP, PEG-100 stearate, cetyl alcohol, and long chain saturated C8-C24 fatty acids. Components found in mild cleansing formulations like directly esterified fatty isethionate may also be included in the compositions of this invention and typically, from 0.01 to 5% by weight.

Emulsion stabilizers generally classified as vegetable based liquids may also be used. Preferred stabilizers are sold under the name Oilwax LC and made available commercially by Lotioncrafter.

Emulsifiers may be present in the composition of the present invention. Total concentration of the emulsifier may range from 0.1 to 40%, and preferably, from 1 to 20%, and most preferably, from 1 to 5% by weight of the composition, including all ranges subsumed therein.

Thickening agents may optionally be included in compositions of the present invention. Particularly useful are the polysaccharides. Examples include starches, natural/synthetic gums and cellulosics. Representative of the starches are chemically modified starches such as sodium hydroxypropyl starch phosphate and aluminum starch octenylsuccinate. Tapioca starch is often preferred. Suitable gums include xanthan, sclerotium, pectin, karaya, arabic, agar, guar, carrageenan, alginate and combinations thereof. Suitable cellulosics include hydroxypropyl cellulose, hydroxypropyl methylcellulose, ethylcellulose and sodium carboxy methylcellulose. Synthetic polymers are yet another class of effective thickening agent. This category includes cross-linked polyacrylates such as the Carbomers, polyacrylamides such as Sepigel® 305 and taurate copolymers such as Simulgel EG® and Aristoflex® AVC, the copolymers being identified by respective INCI nomenclature as Sodium Acrylate/Sodium Acryloyldimethyl Taurate and Acryloyl DimethyltaurateNinyl Pyrrolidone Copolymer. Another preferred synthetic polymer suitable for thickening is an acrylate-based polymer made commercially available by Seppic and sold under the name Simulgel INS100.

Amounts of the thickener, when used, may range from about 0.001 to about 5%, and preferably, from about 0.1 to about 3%, and most preferably, from about 0.2 to about 1.5% by weight of the composition including all ranges subsumed therein.

Other components optionally suitable for use herein include opacifiers like $TiO_2$ and ZnO and colorants like iron oxide red, yellow and black. Such opacifiers and colorants typically have a particle size from 50 nm to 1200 nm, and preferably, from 50 nm to 350 nm.

Colorants, fixatives and abrasives may optionally be included in compositions of the present invention. Each of these substances may range from 0.05 to 5%, preferably between 0.1 and 3% by weight.

Conventional buffers/pH modifiers may be used. These include commonly employed additives like sodium hydroxide, potassium hydroxide, hydrochloric acid, citric acid and citrate/citric acid buffers. In an especially preferred embodiment, the pH of the composition of this invention is from 4 to 8, and preferably, from 4.25 to 7.75, and most preferably, from 6 to 7.5, including all ranges subsumed therein.

Solid/Liquid Cosmetic Benefit Agents

Examples of cosmetic benefit agents (which may be solid or liquid depending on the particular agent's melting point) suitable for use in the inventive compositions, as long as they have the Log P values specified herein, are described below.

One example of suitable solid/liquid agents are humectants. These are generally polyhydric alcohol-type materials. Typical polyhydric alcohols include hexylene glycol, isoprene glycol, propoxylated glycerol, propoxylated methyl glucose ethers such as Glucam P-20 humectant sold by Lubrizol, polypropylene glycol such as PPG425 such as Arcol PPG-425 from Bayer Material Science and mixtures thereof. Most preferred is, propoxylated methyl glucose ethers, polypropylene glycols or a mixture thereof. The amount of humectant employed may range anywhere from 0.5 to 20%, preferably between 1 and 15% by weight of the composition.

To enhance skin moisturization, actives classified as cationic ammonium compounds may optionally be used in the compositions of this invention. Such compounds include salts of hydroxypropyltri ($C_1$-$C_3$ alkyl) ammonium mono-substituted-saccharide, salts of hydroxypropyltri ($C_1$-$C_3$ alkyl) ammonium mono-substituted polyols, dihydroxypropyltri ($C_1$-$C_3$ alkyl) ammonium salts, dihydroxypropyldi ($C_1$-$C_3$ alkyl) mono(hydroxyethyl) ammonium salts, guar hydroxypropyl trimonium salts, 2,3-dihydroxypropyl tri($C_1$-$C_3$ alkyl or hydroxalkyl) ammonium salts or mixtures thereof. In a most preferred embodiment and when desired, the cationic ammonium compound employed in this invention is the quaternary ammonium compound 1,2-dihydroxypropyltrimonium chloride. If used, such compounds typically make up from 0.01 to 30%, and preferably, from 0.1 to 15% by weight of the composition.

When cationic ammonium compounds are used, preferred additional active for use with the same are moisturizing agents such as substituted ureas like hydroxymethyl urea, hydroxyethyl urea, hydroxypropyl urea; bis(hydroxymethyl) urea; bis(hydroxyethyl) urea; bis(hydroxypropyl) urea; N,N'-dihydroxymethyl urea; N,N'-di-hydroxyethyl urea; N,N'-di-hydroxypropyl urea; N,N,N'-tri-hydroxyethyl urea; tetra(hydroxymethyl) urea; tetra(hydroxyethyl) urea; tetra (hydroxypropyl) urea; N-methyl-N'-hydroxyethyl urea; N-ethyl-N,N—N'-hydroxyethyl urea; N-hydroxypropyl-N'-hydroxyethyl urea and N,N'-dimethyl-N-hydroxyethyl urea or mixtures thereof. Where the term hydroxypropyl appears, the meaning is generic for either 3-hydroxy-n-propyl, 2-hydroxy-n-propyl, 3-hydroxy-i-propyl or 2-hydroxy-i-propyl radicals. Most preferred is hydroxyethyl urea.

Amounts of substituted urea, when used, in the composition of this invention range from 0.01 to 20%, and preferably, from 0.5 to 15%, and most preferably, from 2 to 10% based on total weight of the composition and including all ranges subsumed therein.

Yet other suitable examples of solid/liquid agents include fragrances. Fragrances may range from 0.05 to 5%, preferably between 0.1 and 3% by weight.

Other suitable solid/liquid agents may include vitamins and their derivatives. Compositions of the present invention may include vitamins as the desired active. Illustrative vitamins are Vitamin A (retinol) as well as retinol esters like retinol palmitate and retinol propionate, Vitamin $B_2$, Vitamin $B_3$ (niacinamide), Vitamin $B_6$, Vitamin C, Vitamin D, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocotrienol, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight of the composition.

Octadecenedioic acid, azelaic acid, ubiquinone, dihydroxyacetone (DHA) and mixtures thereof may also be used as agents in the composition of this invention. Such compounds, when used, typically make up from 0.2 to 4.5%, and preferably, from 0.5 to 3% by weight of the composition, including all ranges subsumed therein.

Other optional actives agents suitable for use in this invention include resveratrol, resorcinols like 4-butyl resorcinol, 4-ethyl resorcinol, 4-hexyl resorcinol, 4-phenylethyl resorcinol, dimethoxytoluyl propyl resorcinol, 4-cyclopentyl resorcinol, 4-cyclohexylresorcinol, alpha- and/or beta-hydroxyacids, petroselinic acid, conjugated linoleic acid, 4-methoxy salicylic kalium salt, m-tranexamic acid, phenylethyl resorcinol (Symwhite 377 from Symrise), undecylenol phenylalanine (Seppi White from Seppic), 12-hydroxystearic acid, mixtures thereof or the like. Such actives, when used, collectively make up from 0.001 to 12% by weight of the composition.

Desquamation promoters are also suitable cosmetic benefit agents. Illustrative are the alpha-hydroxycarboxylic acids, beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic and its derivatives, lactic and malic acids. Salicylic acid is representative of the beta-hydroxycarboxylic acids. Amounts of these materials when present may range from 0.01 to 15% by weight of the composition.

A variety of herbal extracts may optionally be included as agents in compositions of this invention. The extracts may either be water soluble or water-insoluble carried in a solvent which respectively is hydrophilic or hydrophobic. Water and ethanol are the preferred extract solvents. Illustrative extracts include those from green tea, yarrow, chamomile, licorice, aloe vera, grape seed, citrus unshui, willow bark, sage, thyme and rosemary. Soy extracts may be used and especially when it is desirable to include retinol.

Another example of suitable solid/liquid agents are emollients. These may be in the form of esters and hydrocarbons. Amounts of the emollients may range anywhere from 0.1 to 95%, preferably between 1 and 80%, including all ranges subsumed therein. Among the ester emollients are:

(1) Alkyl esters of saturated fatty acids having 10 to 24 carbon atoms. Examples thereof include behenyl neopentanoate, isopropyl stearate, isopropyl isostearate, isopropyl oleate, isononyl isonanonoate, isopropyl myristate and octyl stearate and mixtures thereof.

(2) Wax esters such as beeswax, spermaceti, myristyl myristate, stearyl stearate; tribehenin wax (3) Hydrocarbons which are suitable include petrolatum, mineral oil, $C_{11}$-$C_{13}$ isoparaffins, and isohexadecane, (4) Sterol esters, of which soya sterol and cholesterol fatty acid esters are examples thereof.

(5) Polypropylene glycol mono and di fatty acid esters such as PPG15 stearyl ethers (6) Diesters of carbonic acid esters such as Cetiol CC also known as dicaprylyl carbonate.

Still further agents suitable for use in this invention include Ceramides (including Ceramide 1, Ceramide 3, Ceramide 3B and Ceramide 6) as well as pseudoceramides. Also optionally suitable for use include materials like $C_{8-22}$ fatty acid substituted saccharides, lipoic acid, retinoxytrimethylsilane (available from Clariant Corp. under the Silcare 1M-75 trademark), dehydroepiandrosterone (DHEA) and combinations thereof. Amounts of these materials may range from 0.000001 to 10%, preferably from 0.0001 to 1% by weight of the composition.

Sunscreen agents may also be included in compositions of the present invention as solid/liquid agents. Particularly preferred are such materials as phenylbenzimidazole sulfonic acid (Ensulizole), ethylhexyl salicylate (octyl salicylate), ethylhexyl p-methoxycinnamate, available as Parsol MCX®, Avobenzene, available as Parsol 1789® and benzophenone-3, also known as Oxybenzone. Also suitable for use is octocrylene. Amounts of the sunscreen agents when present may generally range from 0.1 to 30%, preferably from 0.5 to 20%, optimally from 0.75 to 10% by weight.

Other examples of a suitable solid/liquid agent are preservatives. Preservatives can desirably be incorporated into the compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are iodopropynyl butyl carbamate, phenoxyethanol, caprylyl glycol, $C_{1-6}$ parabens (especially, methyl paraben and/or propyl paraben), imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from 0.01% to 2% by weight of the composition, including all ranges subsumed therein. An especially preferred combination is octocrylene and caprylyl glycol, since caprylyl glycol has been disclosed to enhance UVA and UVB protection.

Antimicrobials such as Triclosan may also be an example of a suitable solid agent.

Viscosity of the composition is in general in the range of from 0.1 Pas to 500 Pas, preferably from 0.5 Pas to 200

Pas—(as measured using a Brookfield DV-I+viscometer (20RPM, RV6, 30 seconds, 25° C.).

Solid agents suitable for use herein typically have partition coefficients from −5 to 15, preferably from −3 to 12, and most preferably from −2 to 10, including all ranges subsumed therein. Liquid agents suitable for use herein typically have partition coefficients from −0.75 to 15, preferably from −0.5 to 12, and most preferably from −0.25 to 10, including all ranges subsumed therein.

Most preferred solid agents suitable for use in this invention include solid benefit agents like climbazole, ensulizole, butylmethoxy dibenzoylmethane, terephthalyidene dicamphor sulfonic acid (Mexoryl), cholesterol, niacinamide, 12-hydroxystearic acid, glycolic acid, 2-hydroxyethyl urea, salicylic acid, polychloro phenoxy phenol, flavonoids like quercitin, petrolatum, solid retinol derivatives such as retinyl palmitate, acetylglucosamine, undecyleroyl phenylalamine, dicarboxylic acids like octadecenedioic acid, $C_{4-6}$ resorcinols, Vitamin D and its derivatives, dicaprylyl carbonate, caprylyl glycol, $C_{1-6}$ parabens, mixtures thereof or the like.

Most preferred liquid agents suitable for use in this invention include liquid benefit agents like, mineral oil, conjugated linoleic acid, petroselinic acid, isopropyl myristate, ethylhexyl salicyclate, caprylic/capric triglyceride, liquid retinol derivatives such as retinol propionate, octocrylene, methoxycrylene, octyl methoxycinnamate, PPG-20 methyl glucose ether (Glucam™ P-20 Humectant), polypropylene glycol such as PPG-425, mixtures thereof or the like.

Partition coefficients (Log $P_{o/w}$) values and melting temperature for some solid and liquid agents suitable for inventive cosmetic compositions are listed in tables 1 and table 2 below.

TABLE 1

| Solid Cosmetic agent | Log $P_{o/w}$ | Tm (° C.) |
|---|---|---|
| Climbazole | 3.49 | 98-99 |
| Avobenzone | 4.19 | 80-85 |
| Niacinamide | −0.37 | 128 |
| 12-Hydroxystearic acid | 5.77 | 75-80 |
| cholesterol | 9.62 | 148 |
| Glycolic acid | −1.2 | 75 |
| 2-hydroxyethyl urea | −0.86 | 164-169 |
| Salicylic Acid | 2.01 | 159 |
| Triclosan | 5.34 | 55 |
| Quercitin | 1.99 | 316 |
| Methyl Paraben | 1.88 | 131 |

TABLE 2

| Liquid Cosmetic agent | Log $P_{o/w}$ |
|---|---|
| Octylmethoxycinnamate | 5.92 |
| Isopropyl myristate | 7.25 |
| PPG-425 | 0.21 |
| octocrylene | 6.89 |
| isopropyl isostearate | 9.14 |
| Pelemol GTIS, TISC, . . . | >6 |
| Glucam P-20 (PPG20 methyl glucose ether) | <1 |
| Mineral Oil | >6 |
| Conjugated linoleic acid | >6 |

In the invention, the weight ratio of the solid agent to the liquid agent (based on total weight of the solid agent and liquid agent in the composition being assessed) is in the range from 0.001 to 1, and preferably, from 0.001 to 0.9, and most preferably, from 0.01 to 0.8, including all ranges subsumed therein. Within this range the solubility of the solid agent in the liquid agent is enhanced in the presence of the tricyclodecane amide, even if the solid agent is somewhat soluble in the liquid agent in the absence of the tricylodecane amide.

A wide variety of packaging can be employed to store and deliver the composition of this invention. Packaging is often dependent upon the type of personal care end-use. For instance, leave-on skin lotions and creams, shampoos, conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Metallic cans pressurized by a propellant and having a spray nozzle serve as packaging for antiperspirants, shave creams and other personal care products.

The following examples are provided to facilitate an understanding of the present invention. The examples are not intended to limit the scope of the claims.

EXAMPLES

Experimental Methods

All reagents and solvents were obtained from commercial sources (Sigma-Aldrich, EMD Chemicals) and used as supplied unless otherwise indicated. Parallel reactions and parallel solvent removal were performed using a Buchi Syncore reactor (Buchi Corporation, New Castle, Del.). Reaction monitoring was performed using thin layer chromatography (TLC). TLC was performed using silica gel 60 F254 plates (EMD Chemicals) and visualizing by UV (254 nm), 4% phosphomolybdic acid (PMA) in ethanol (EtOH), 4% ninhydrin in ethanol and/or using an iodine chamber. Flash chromatography (FC) was performed using a Biotage SP4 system (Biotage LLC, Charlottesville, Va.). High performance liquid chromatography (HPLC) was performed using a Waters 2695 Separations Module equipped with a Waters 2996 Photodiode Array Detector and operated with Empower Pro software (Waters Corp.). Separations were carried out at 1 ml/min on a Restek Pinnacle DB C18 column (5 μm, 4.6×150 mm) maintained at 30° C. Examples for HPLC were prepared by dissolving 1 mg of example in 1 ml mobile phase A:B (1:1) and injecting 5 μL onto the column. The mobile phase consisted of A=0.1% trifluoroacetic acid (TFA) in water and B=0.1% TFA in acetonitrile (ACN) operated using gradient elution from 95:5 A:B to 5:95 A:B (gradient, 25 min) followed by 100% B (isocratic, 5 min). Gas Chromatography (GC) was performed using an Agilent 7890A Gas Chromatograph equipped with an Agilent DB-5HT (15 m×0.32 mm; 0.1μ) column and an FID detector heated at 325° C. Examples were prepared at 25 ppm concentrations in acetone and the injection volume was 1 μL. The air, helium and hydrogen flows were maintained at 400, 25 and 30 ml/min and the separation gradient consisted of 100° C. (isothermal, 1 min), 15° C./min up to 250° C., 250° C. (isothermal, 4 min), 25° C./min up to 300° C., and 300° C. (isothermal, 3 min). Liquid chromatography/mass spectrometry (LC-MS) was performed using a Finnigan Mat LCQ Mass Spectrometer via direct infusion of examples (50 ppm) in methanol and the total ion count monitored using electrospray ionization in the (+) mode (ESI+). 1H and 13C Nuclear magnetic resonance (NMR) spectroscopy was performed using a Eft-60 NMR Spectrometer (Anasazi instruments, Inc.) and processed using WinNuts software (Acorn NMR, Inc.). Melting points were determined using a Meltemp apparatus (Laboratory Devices). Purity was determined by HPLC-UV/Vis and/or GC. All compounds were unequivocally confirmed by LC-MS and/or $^1$H NMR. DCM=Dichloromethane; DIPEA=N,N-Diisopropylethylamine; RT=room temperature; MTBE=Methyl tert-Butyl ether; TFA=Trifluroacetic acid; ACN=acetonitrile; IPA=isopropyl alcohol; FC=flash chromatography.

Examples 1 through 28 as shown demonstrate the synthesis of tricyclodecane amides suitable for use in this invention.

General Procedure

Tricyclo[3.3.1.1$^{3,7}$]decane-1-carbonyl chloride was stirred under nitrogen atmosphere in Dichloromethane and the solution was cooled to 0° C. in an ice bath. A solution of a chosen amine was slowly added to the solution of Tricyclo[3.3.1.1$^{3,7}$]decane-1-carbonyl chloride. Upon completion of addition the reaction mixture was warmed up to room temperature and stirred under N$_2$ overnight. Work up-: water was added to the reaction mixture and was extracted with dichlromethane, washed with 0.1 N HCl, water, sat. NaHCO$_3$ and sat. NaCl solution, dried over Sodium sulfate and evaporated on the rotovap. The solid was purified by a silica gel filtration (silica gel bed, used 15% ethyl acetate in hexane). The filtrate was evaporated on the rotovap, to give pure white crystalline corresponding amides.

Example 1

Synthesis of Methanone, (3,3-dimethyl-1-piperidinyl)tricyclo[3.3.1.1$^{3,7}$]dec-1-yl (Compound C11)

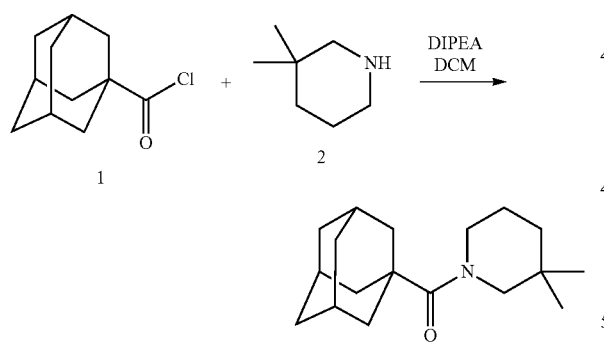

DIPEA (144 µL, 0.8 mmol) was added to a solution of Tricyclo[3.3.1.1$^{3,7}$]decane-1-carbonyl chloride (1) (150 mg, 0.8 mmol) and 3,3-dimethylpiperidine (2) (85 mg, 0.8 mmol) in DCM (2 ml) and the solution stirred at room temperature for 1 hour. At this time, TLC [15:85 EA:hexane, 20 µL aliquot into MTBE:1 N HCl (400 µL:400 µL)] showed the formation of a single product. The reaction mixture was allowed to stir for and additional 16 hours. The solution was diluted with CHCl$_3$ (10 ml), washed with 1N HCl (10 ml), saturated NaHCO$_3$ (10 ml), dried (Na$_2$SO$_4$), filtered and the solvents removed to give crude product as a colorless oil (160 mg). The product was further purified by FC on silica gel using 15:85 EA:hexane to give the desired product as a white solid.

Example 2

Synthesis of Methanone, (decahydroisoquinolinyl)tricyclo[3.3.1.1$^{3,7}$]dec-1-yl-(C9)

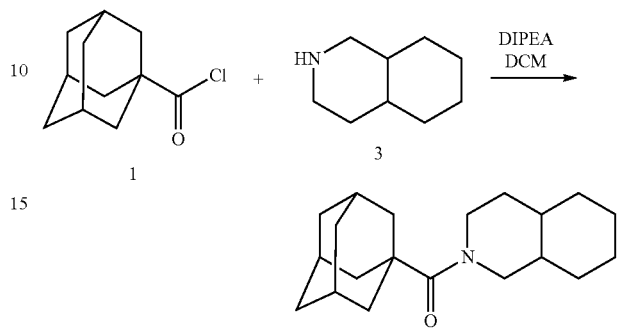

DIPEA (1.93 ml, 11.1 mmol) was added to a solution of Tricyclo[3.3.1.1$^{3,7}$]decane-1-carbonyl chloride (1) (2 g, 10.1 mmol) and decahydroisoquinoline (3) (1.59 ml, 11.1 mmol) in DCM (20 ml) and the solution stirred at room temperature for 4 hours. At this time, TLC [15:85 EA:hexane, 20 µL aliquot into MTBE:1 N HCl (400 µL:400 µL)] showed the formation of a single product. The solution was washed with 0.1 N HCl (30 ml), saturated NaHCO$_3$ (30 ml), dried (Na$_2$SO$_4$), filtered and the solvents removed to give crude product which was further purified by FC on silica gel using 15:85 EA:hexane to give the desired product as a white solid.

Example 3

Synthesis of Methanone, (4,4-dimethyl-1-piperidinyl)tricyclo[3.3.1.1$^{3,7}$]dec-1-yl

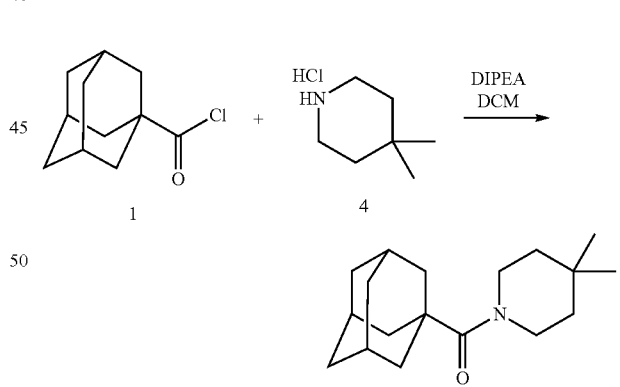

DIPEA (1.93 ml, 11.1 mmol) was added to a solution of Tricyclo[3.3.1.1$^{3,7}$]decane-1-carbonyl chloride (1) (1 g, 5.5 mmol) and 4,4-dimethylpiperidine hydrochloride (4) (828 mg, 5.5 mmol) in DCM (10 ml) and the solution stirred at room temperature for 4 hours. At this time, TLC [15:85 EA:hexane, 20 µL aliquot into MTBE:1 N HCl (400 µL:400 µL)] showed the formation of a single chemical. The solution was washed with 0.1 N HCl (30 ml), saturated NaHCO$_3$ (30 ml), dried (Na$_2$SO$_4$), filtered and the solvents removed to give crude product which was further purified by FC on silica gel using 15:85 EA:hexane to give the desired product as a crystalline white solid.

Example 4

Synthesis of Methanone, (cyclopentylaminyl)tricyclo[3.3.1.1$^{3,7}$]dec-1-yl

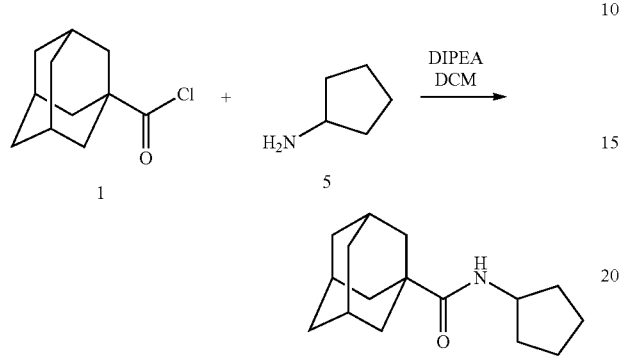

DIPEA (1.93 ml, 11.1 mmol) was added to a solution of Tricyclo[3.3.1.1$^{3,7}$]decane-1-carbonyl chloride (1) (2 g, 10.1 mmol) and cyclopentylamine (5) (1.09 ml, 11.1 mmol) in DCM (20 ml) and the solution stirred at room temperature for 4 hours. At this time, TLC [15:85 EA:hexane, 20 μL aliquot into MTBE:1 N HCl (400 μL:400 μL)] showed the formation of a single product. The solution was washed with 0.1N HCl (30 ml), saturated NaHCO$_3$ (30 ml), dried (Na$_2$SO$_4$), filtered and the solvents removed to give crude product which was further purified via crystallization from 15% EA in hexanes to give the desired product as a white solid.

Example 5

Synthesis of Methanone, (4-methyl-1-piperidinyl) tricyclo[3.3.1.1$^{3,7}$]dec-1-yl (Compound C13)

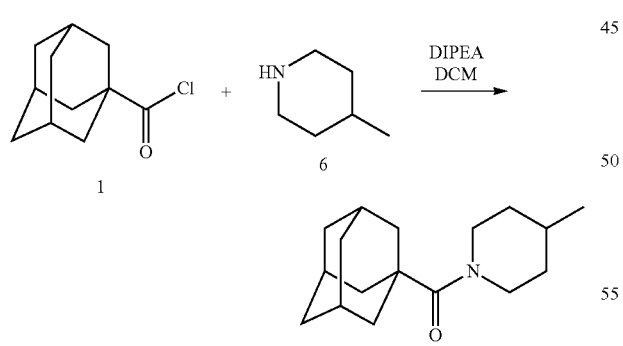

DIPEA (1.93 ml, 11.1 mmol) was added to a solution of Tricyclo[3.3.1.1$^{3,7}$]decane-1-carbonyl chloride (1) (1 g, 5.5 mmol) and 4-methylpiperidine (6) (1.27 ml, 11.1 mmol) in DCM (20 ml) and the solution stirred at room temperature for 4 hours. At this time, TLC [15:85 EA:hexane, 20 μL aliquot into MTBE:1 N HCl (400 μL:400 μL)] showed the formation of a single product. The solution was washed with 0.1 N HCl (30 ml), saturated NaHCO$_3$ (30 ml), dried (Na$_2$SO$_4$), filtered and the solvents removed to give crude product which was further purified by FC on silica gel using 15:85 EA:hexane to give the desired product as a white solid.

Example 6

Synthesis of Methanone, (3-methyl-1-piperidinyl) tricyclo[3.3.1.1$^{3,7}$]dec-1-yl (Compound C14)

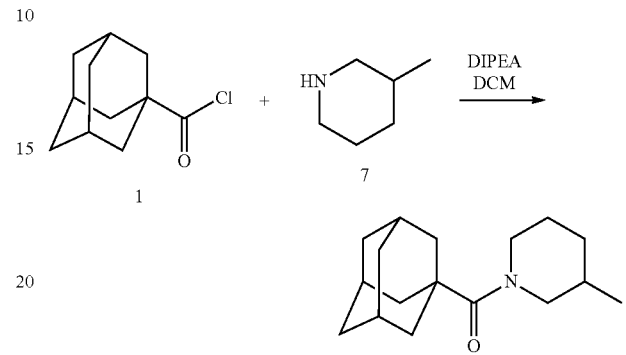

DIPEA (1.93 ml, 11.1 mmol) was added to a solution of Tricyclo[3.3.1.1$^{3,7}$]decane-1-carbonyl chloride (1) (1 g, 5.5 mmol) and 3-methylpiperidine (7) (1.31 ml, 11.1 mmol) in DCM (20 ml) and the solution stirred at room temperature for 4 hours. At this time, TLC[15:85 EA:hexane, 20 μL aliquot into MTBE:1 N HCl (400 μL:400 μL)] showed the formation of a single product and some SM remaining. The solution was washed with 0.1N HCl (30 ml), saturated NaHCO$_3$ (30 ml), dried (Na$_2$SO$_4$), filtered and the solvents removed to give crude product which was further purified by FC on silica gel using 15:85 EA:hexane to give the desired product as a white solid.

Example 7

Synthesis of Methanone, (4-amido-piperidinyl)tricyclo[3.3.1.1$^{3,7}$]dec-1-yl-(Compound C7)

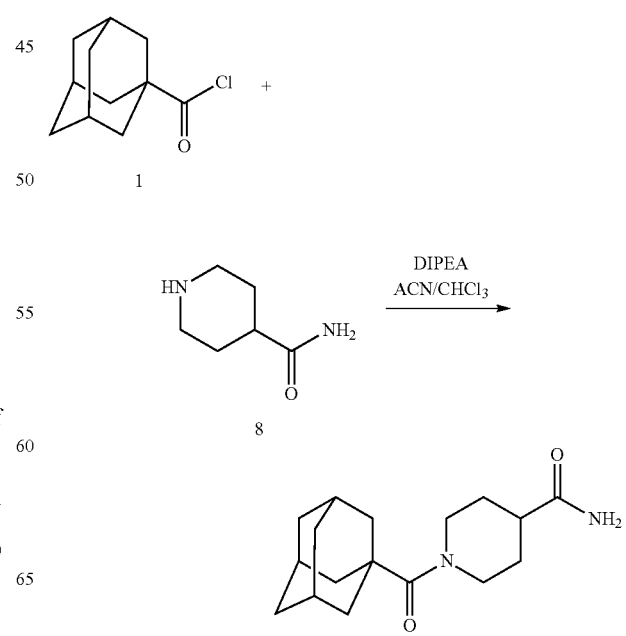

4-Piperidinecarboxamide (8) (71 mg, 0.6 mmol) was dissolved in ACN:CHCl₃ (3 ml, 1:1) solution by gentle warming. DIPEA (96 µL, 0.6 mmol) was added, followed by Tricyclo[3.3.1.1$^{3,7}$]decane-1-carbonyl chloride (1) (100 mg, 0.5 mmol) and the solution stirred at room temperature for 20 hours. At this time, TLC [7% MeOH in CHCl₃, 20 µL aliquot into MTBE:1 N HCl (400 µL:400 µL)] showed the formation of a single product. The solution was diluted with 15% IPA in CHCl₃ (8 ml), washed with 0.1N HCl (8 ml), saturated NaHCO₃ (8 ml), dried (Na₂SO₄), filtered and the solvents removed to give crude product which was further purified by FC on silica gel using 7% MeOH in CHCl₃ to give product as a white solid.

Example 8

Synthesis of Methanone, (3-cyano-piperidinyl)tricyclo[3.3.1.1$^{3,7}$]dec-1-yl

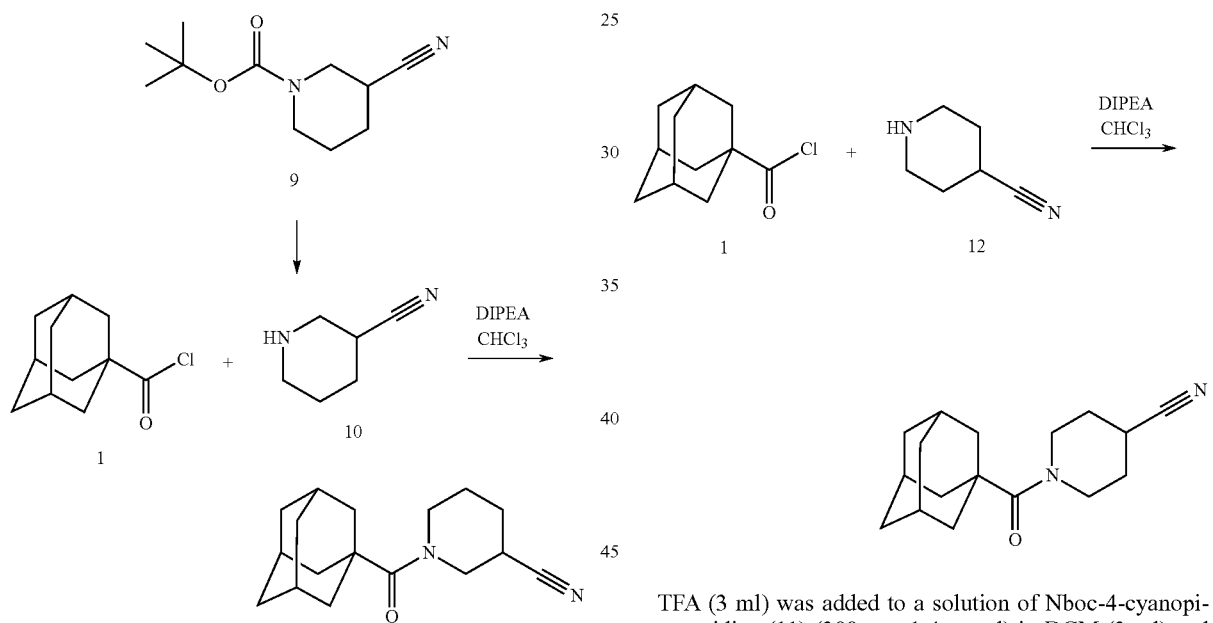

TFA (3 ml) was added to a solution of Nboc-3-cyanopiperidine (9) (300 mg, 1.4 mmol) in DCM (3 ml) and stirred at room temperature for 1 hour. The solvents were removed in vacuo and the residue dissolved in 15% IPA in CHCl3 (8 ml), washed with 1N NaOH: saturated NaCl sol'n (8 ml, 1:1), dried (Na₂SO₄), filtered and the solvents removed to give 3-cyanopiperidine (10) (141 mg, 90% yield) which was used crude for the next step. Tricyclo[3.3.1.1$^{3,7}$]decane-1-carbonyl chloride (1) (100 mg, 0.5 mmol) was added to a solution of 3-cyanopiperidine (10) (61 mg, 0.6 mmol) and DIPEA (96 µL, 0.6 mmol) in CHCl₃ (1 ml) and the solution stirred at room temperature for 16 hours. At this time, TLC [40:60 EA:hexane, 20 µL aliquot into MTBE:1 N HCl (400 µL:400 µL)] showed the formation of a major product. The solution was diluted with CHCl₃ (8 ml), washed with 0.1N HCl (8 ml), saturated NaHCO₃ (8 ml), dried (Na₂SO₄), filtered and the solvents removed to give crude product which was further purified by FC on silica gel using 40:60 EA: hexane to give product as a white solid.

Example 9

Synthesis of Methanone, (4-cyano-piperidinyl)tricyclo[3.3.1.1$^{3,7}$]dec-1-yl (Compound C6)

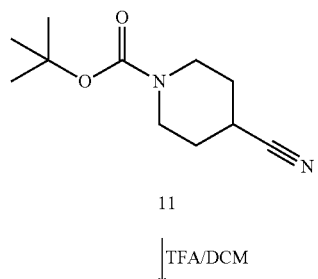

TFA/DCM

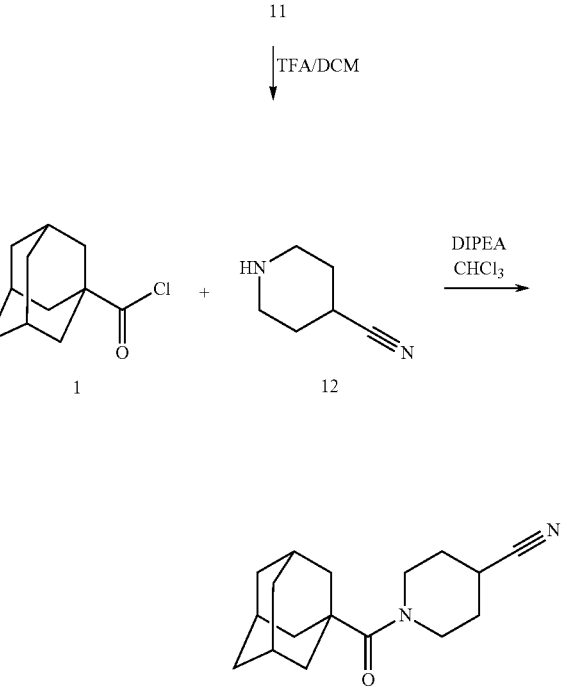

TFA (3 ml) was added to a solution of Nboc-4-cyanopiperidine (11) (300 mg, 1.4 mmol) in DCM (3 ml) and stirred at room temperature for 1 hour. The solvents were removed in vacuo and the residue dissolved in 15% IPA in CHCl3 (8 ml), washed with 1N NaOH: saturated NaCl sol'n (8 ml, 1:1), dried (Na₂SO₄), filtered and the solvents removed to give 4-cyanopiperidine (12) (141 mg, 90% yield) which was used crude for the next step. Tricyclo[3.3.1.1$^{3,7}$]decane-1-carbonyl chloride (1) (230 mg, 1.2 mmol) was added to a solution of 4-cyanopiperidine (12) (140 mg, 1.3 mmol) and DIPEA (222 µL, 1.3 mmol) in CHCl₃ (2 ml) and the solution stirred at room temperature for 16 hours. At this time, TLC [40:60 EA:hexane, 20 µL aliquot into MTBE:1 N HCl (400 µL:400 µL)] showed the formation of a major product. The solution was diluted with CHCl₃ (8 ml), washed with 0.1 N HCl (8 ml), saturated NaHCO₃ (8 ml), dried (Na₂SO₄), filtered and the solvents removed to give crude product which was further purified by FC on silica gel using 40:60 EA:hexane to give product as a white solid.

Example 10

Synthesis of Methanone, (1,1-dimethyl-3,3-dimethylbutylaminyl) tricyclo[3.3.1.1³,⁷]dec-1-yl-(Compound C21)

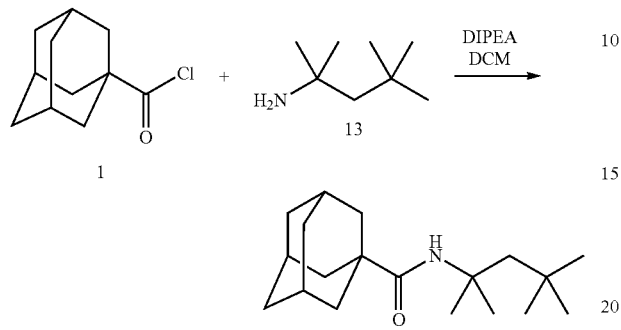

Tricyclo[3.3.1.1³,⁷]decane-1-carbonyl chloride (1) (300 mg, 1.5 mmol) was stirred under nitrogen atmosphere in DCM (3 mL) and the solution was cooled to 0° C. in an ice bath. DIPEA (300 µL, 1.7 mmol) and 1,1-dimethyl-3,3-dimethylbutylamine (13) (271 µL, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. The reaction was diluted with DCM and washed sequentially with 0.1 N HCl, water, saturated NaHCO₃, saturated NaCl, dried (Na₂SO₄), filtered and the solvents removed to give crude product which was purified by FC on silica gel using 15% EA in hexane to give product as a white solid.

Example 11

Synthesis of Methanone, (3,3-dimethylbutylaminyl) tricyclo[3.3.1.1³,⁷]dec-1-yl-(Compound C19)

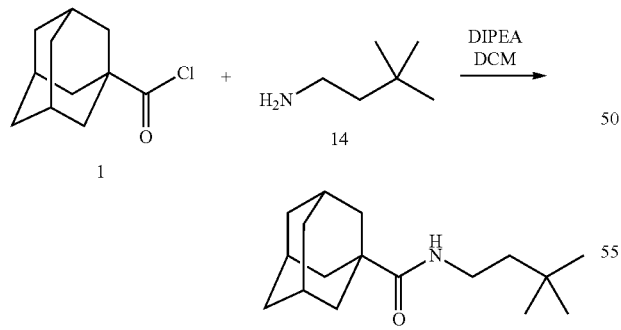

Tricyclo[3.3.1.1³,⁷]decane-1-carbonyl chloride (1) (300 mg, 1.5 mmol) was stirred under nitrogen atmosphere in DCM (3 mL) and the solution to 0° C. in an ice bath. DIPEA (300 µL, 1.7 mmol) and 3,3-dimethylbutylamine (14) (228 µL, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. The reaction was diluted with DCM and washed sequentially with 0.1 N HCl, water, saturated NaHCO₃, saturated NaCl, dried (Na₂SO₄), filtered and the solvents removed to give crude product which was purified by FC on silica gel using 15% EA in hexane to give product as a white solid.

Example 12

Synthesis of Methanone, (decahydroquinolinyl) tricyclo[3.3.1.1³,⁷]dec-1-yl-(Compound C10)

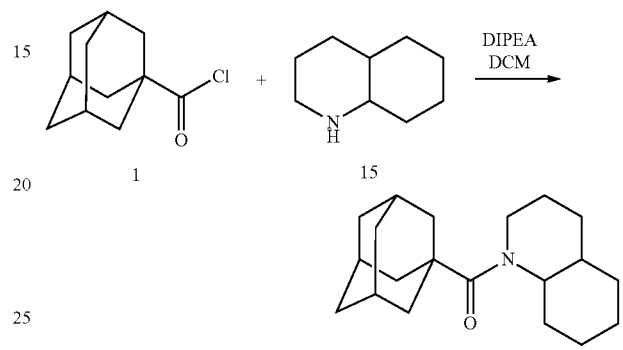

Tricyclo[3.3.1.1³,⁷]decane-1-carbonyl chloride (1) (40.0 g, 0.200 moles) was stirred under nitrogen atmosphere in DCM (340 mL, 1.2 M) and the solution cooled to 0° C. in an ice bath. DIPEA (27.3 g, 18.44 mL, 0.210 moles) and decahydroquinoline (15) (28.35 g, 30.28 mL, 0.210 moles) were mixed and added to the Tricyclo[3.3.1.13,7]decane-1-carbonyl chloride solution slowly. The reaction mixture was allowed to warm up to room temperature and stirred under nitrogen for 16 hours. The reaction was diluted with DCM and washed sequentially with 0.1 N HCl, water, saturated NaHCO₃, saturated NaCl, dried (Na₂SO₄), filtered and the solvents removed to give crude product which was purified on silica gel (filtration through a 3" bed of silica gel) using 15:85 EA:hexane to give product as a white crystalline solid.

Example 13

Synthesis of Methanone, (TRANS-decahydroquinolinyl)tricyclo[3.3.1.1³,⁷]dec-1-yl

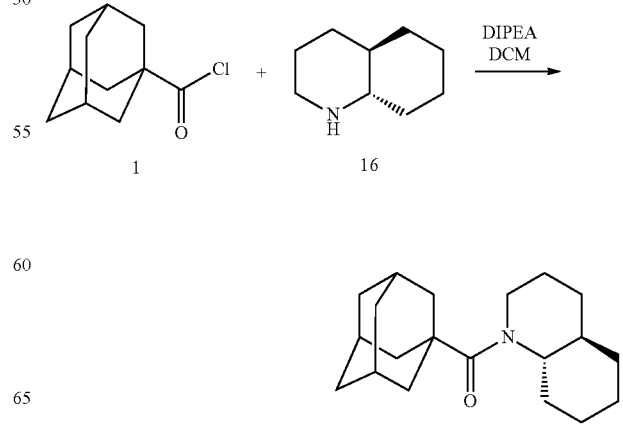

Tricyclo[3.3.1.1$^{3,7}$]decane-1-carbonyl chloride (1) (200 mg, 1 mmoles) was added to a solution of trans-decahydroquinoline (16) (154 mg, 1.1 mmoles) and DIPEA (193 µL, 1.1 mmoles) in CHCl$_3$ (2 ml) and the solution stirred at room temperature for 16 hours. The reaction mixture was diluted with CHCl$_3$ (8 ml) and washed sequentially with 0.1 N HCl, saturated NaHCO$_3$, dried (Na$_2$SO$_4$), filtered and the solvents removed to give crude product which was purified by FC on silica gel using 7% EA in hexane to give product as a white solid.

Example 14

Methanone, (azetidinyl)tricyclo[3.3.1.1$^{3,7}$]dec-1-yl- (Compound C4)

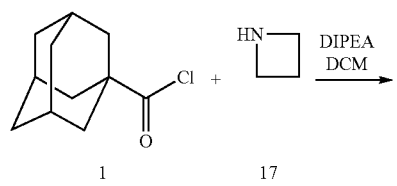

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (540 µL, 3.1 mmol) and azetidine hydrochloride (17) (148 mg, 1.6 mmol) were mixed and added to the Tricyclo[3.3.1.13,7]decane-1-carbonyl chloride solution slowly. The reaction mixture was allowed to warm up to room temperature and stirred under nitrogen for 16 hours. EA:water (10 ml; 1:1) was added, the organic layer separated and the aqueous layer washed with EA (5 ml). The combined organic layers were sequentially washed with 0.1 N HCl, water, saturated NaHCO$_3$, saturated NaCl, dried (Na$_2$SO$_4$), filtered and the solvents removed to give crude product which was purified by FC on silica gel using 15-25% EA in hexane to give product as a white solid.

Example 15

Synthesis of Methanone, (pyrrolidinyl)tricyclo [3.3.1.1$^{3,7}$]dec-1-yl

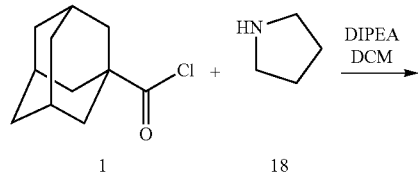

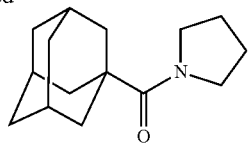

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and pyrrolidine (18) (131 µL, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. The obtained precipitate was filtered and washed with 1 N HCl, water and dried under high vacuum. The crude product was purified over a silica gel bed to give product as a white solid (334 mg, 95%).

Example 16

Synthesis of Methanone, (hexahydroazepinyl)tricyclo[3.3.1.1$^{3,7}$]dec-1-yl-(Compound C5)

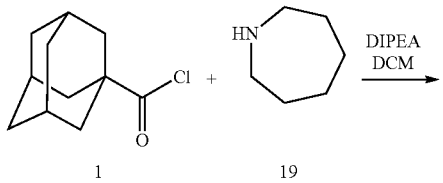

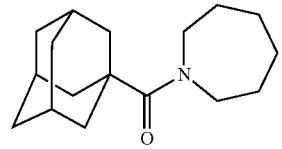

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and azepane (19) 192 µL, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. EA was added and the organic layer washed with 1N HCl, saturated NaCl, dried (Na$_2$SO$_4$), filtered and the solvents removed to give crude product which was purified by FC on silica gel using 15:85 EA:hexane to give product as a white solid.

Example 17

Synthesis of Methanone, (2-methyl-1-piperidinyl) tricyclo[3.3.1.1$^{3,7}$]dec-1-yl-(Compound C12)

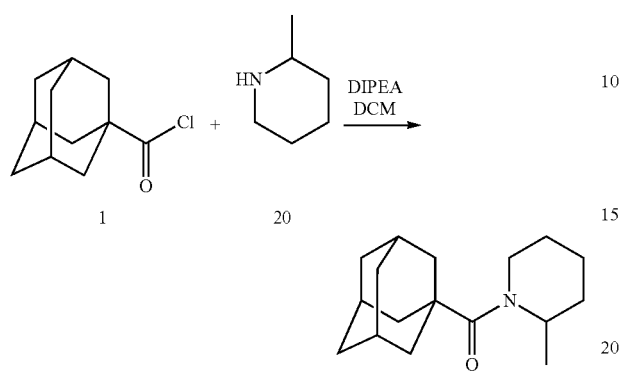

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and 2-methylpiperidine (20) (216 mg, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. EA was added and the organic layer washed with 1N HCl, saturated NaCl, dried (Na$_2$SO$_4$), filtered and the solvents removed to give crude product which was purified by FC on silica gel using 15:85 EA:hexane to give product as a white solid.

Example 18

Synthesis of Methanone, (3,5-dimethyl-1-piperidinyl)tricyclo[3.3.1.1$^{3,7}$]dec-1-yl-(Compound C15)

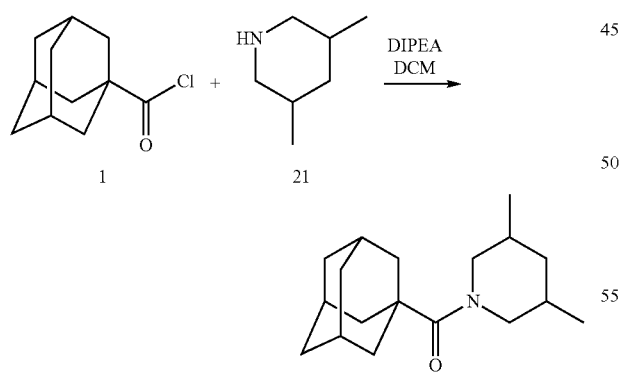

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and 3,5-dimethylpiperidine (21) (226 µL, 1.7 mmol) were mixed and added to the Tricyclo[3.3.1.1$^{3,7}$]decane-1-carbonyl chloride solution slowly. The reaction mixture was allowed to warm up to room temperature and stirred under nitrogen for 16 hours. Water was added, the organic layer separated and the aqueous layer washed with DCM (5 ml). The combined organic layers were sequentially washed with 0.1 N HCl, water, saturated NaHCO$_3$, saturated NaCl, dried (Na$_2$SO$_4$), filtered and the solvents removed to give crude product which was purified by FC on silica gel using 12:88 EA:hexane to give product as a white solid.

Example 19

Synthesis of Methanone, (4-methyl-4-ethy-piperidinyl)tricyclo[3.3.1.1$^{3,7}$]dec-1-yl-(Compound 016)

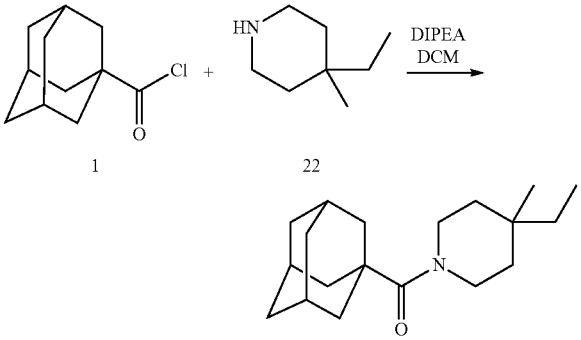

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and 4-ethyl-4-methylpiperidine (22) (216 mg, 1.7 mmol) were mixed and added to the Tricyclo[3.3.1.1$^{3,7}$]decane-1-carbonyl chloride solution slowly. The reaction mixture was allowed to warm up to room temperature and stirred under nitrogen for 16 hours. Water was added, the organic layer separated and the aqueous layer washed with DCM (5 ml). The combined organic layers were sequentially washed with 0.1 N HCl, water, saturated NaHCO$_3$, saturated NaCl, dried (Na$_2$SO$_4$), filtered and the solvents removed to give crude product which was purified by FC on silica gel using 12:88 EA:hexane to give product as a white solid.

Example 20

Synthesis of Methanone, (3,3-diethyl-pyrrolidinyl) tricyclo[3.3.1.1$^{3,7}$]dec-1-yl-(Compound C17)

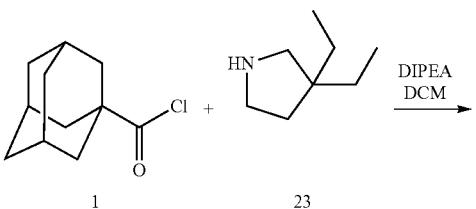

27
-continued

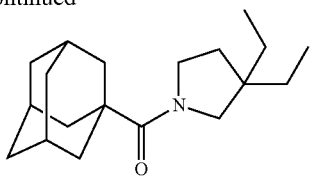

Tricyclo[3.3.1.1³,⁷]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and 3,3-diethyl-pyrrolidine (23) (216 mg, 1.7 mmol) were mixed and added to the Tricyclo[3.3.1.1³,⁷]decane-1-carbonyl chloride solution slowly. The reaction mixture was allowed to warm up to room temperature and stirred under nitrogen for 16 hours. EA was added and the organic layer washed with 1N HCl, saturated NaCl, dried (Na₂SO₄), filtered and the solvents removed to give crude product which was purified by FC on silica gel using 15:85 EA:hexane to give product as a white solid.

Example 21

Synthesis of Methanone, (cyclobutylaminyl)tricyclo[3.3.1.1³,⁷]dec-1-yl

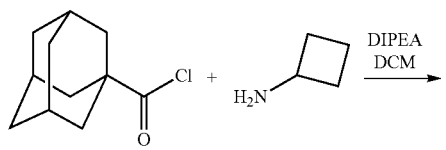

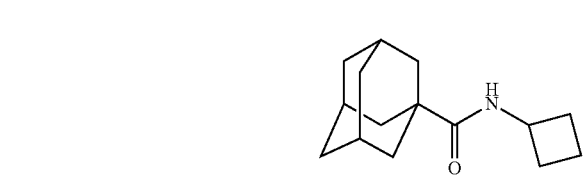

Tricyclo[3.3.1.1³,⁷]decane-1-carbonyl chloride (1) (300 mg, 1.6 mmol) was stirred under nitrogen atmosphere in DCM (3 mL) and the solution cooled to 0° C. in an ice bath. DIPEA (300 L, 1.7 mmol) and cyclobutylamine (24) (150 µL, 1.7 mmol) were mixed and added to the Tricyclo[3.3.1.13,7]decane-1-carbonyl chloride solution slowly. The reaction mixture was allowed to warm up to room temperature and stirred under nitrogen for 16 hours. The obtained precipitate was filtered and washed with 1 N HCl, water and dried under high vacuum. The crude product was purified over a silica gel bed to give product as a white solid.

28

Example 22

Synthesis of Methanone, (2,2-dimethylpropylaminyl) tricyclo[3.3.1.1³,⁷]dec-1-yl-(Compound C20)

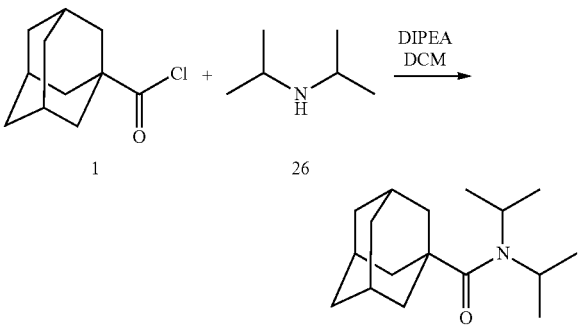

Tricyclo[3.3.1.1³,⁷]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and 2,2-dimethylpropylamine (25) (150 µL, 1.7 mmol) were mixed and added to the Tricyclo[3.3.1.1³,⁷]decane-1-carbonyl chloride solution slowly. The reaction mixture was allowed to warm up to room temperature and stirred under nitrogen for 16 hours. The obtained precipitate was filtered and washed with water and dried under high vacuum. The crude product was purified over a silica gel bed to give product as a white solid.

Example 23

Synthesis of Methanone, (N,N-diisopropyl) tricyclo[3.3.1.1³,⁷]dec-1-yl-(Compound C18)

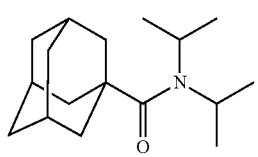

Tricyclo[3.3.1.1³,⁷]decane-1-carbonyl chloride (1) (300 mg, 1.6 mmol) was stirred under nitrogen atmosphere in DCM (3 mL) and the solution cooled to 0° C. in an ice bath. DIPEA (300 µL, 1.7 mmol) and diisopropylamine (26) (232 µL, 1.7 mmol) were mixed and added to the Tricyclo[3.3.1.13,7]decane-1-carbonyl chlorides solution slowly. The reaction mixture was allowed to warm up to room temperature and stirred under nitrogen for 16 hours. The obtained precipitate was filtered and washed with EA. The filtrates were combined and sequentially washed with 0.1 N HCl, water, saturated NaHCO$_3$, saturated NaCl, dried (Na$_2$SO$_4$), filtered and the solvents removed to give crude product which was purified by FC on silica gel using 20:80 EA:hexane to give product as a white solid.

Example 24

Synthesis of Methanone, (1,3-dimethyl-butylaminyl) tricyclo[3.3.1.1$^{3,7}$]dec-1-yl-(Compound C22)

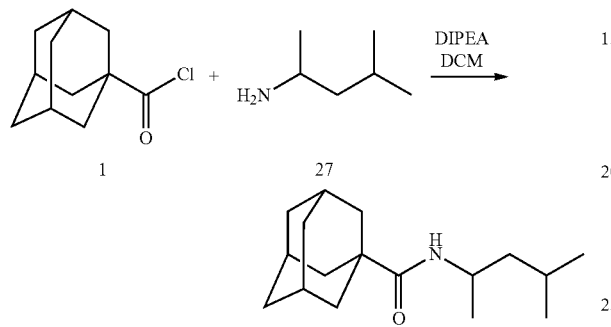

Tricyclo[3.3.1.1$^{3,7}$]decane-1-carbonyl chloride (1) (300 mg, 1.6 mmol) was stirred under nitrogen atmosphere in DCM (4 mL) and the solution cooled to 0° C. in an ice bath. DIPEA (300 μL, 1.7 mmol) and 1,3-dimethylbutylamine (27) (239 μL, 1.7 mmol) were mixed and added to the Tricyclo[3.3.1.1$^{3,7}$]decane-1-carbonyl chloride solution slowly. The reaction mixture was allowed to warm up to room temperature and stirred under nitrogen for 16 hours. The obtained precipitate was filtered and washed with water and dried under high vacuum. The crude product was purified over a silica gel bed to give product as a white solid.

Example 25

Synthesis of Methanone, (Tricyclo[3.3.1.1$^{3,7}$]decanyl)-N-tricyclo[3.3.1.1$^{3,7}$]dec-1-yl-(Compound C8)

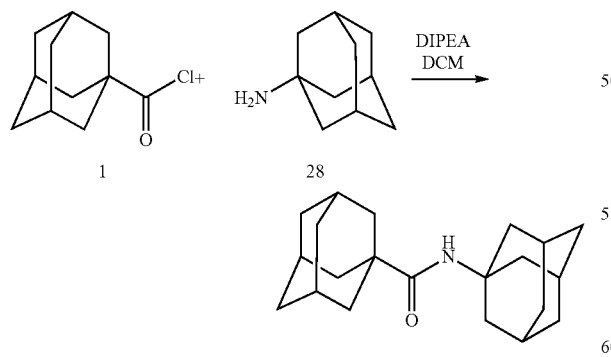

Tricyclo[3.3.1.1$^{3,7}$]decane-1-carbonyl chloride (1) (300 mg, 1.6 mmol) was stirred under nitrogen atmosphere in DCM (3 mL) and the solution cooled to 0° C. in an ice bath. DIPEA (300 μL, 1.7 mmol) and Tricyclo[3.3.1.1$^{3,7}$]decan-1-amine (28) (257 mg, 1.7 mmol) were mixed and added to the Tricyclo[3.3.1.13,7]de- cane-1-carbonyl chloride solution slowly. The reaction mixture was allowed to warm up to room temperature and stirred under nitrogen for 16 hours. The obtained precipitate was filtered and washed with water and dried under high vacuum. The crude product was purified by FC on silica gel using 15:85 EA:hexane containing 0.1% DIPEA, followed by elution with CHCl$_3$ to give product as a white solid.

Example 26

Methanone, (3-aminotetrahydrofuranyl)tricyclo [3.3.1.1$^{3,7}$]dec-1-yl

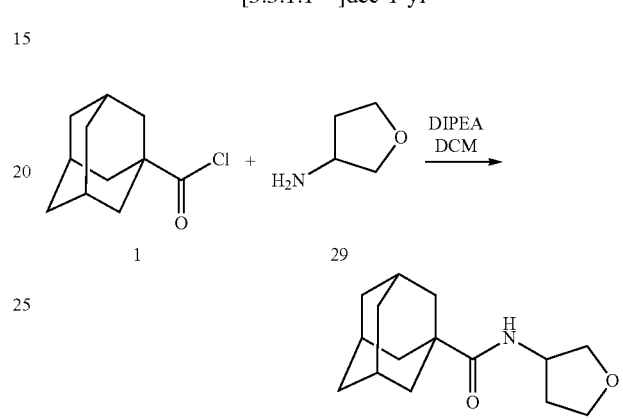

DIPEA (1.93 ml, 11.1 mmol) was added to a solution of Tricyclo[3.3.1.1$^{3,7}$]decane-1-carbonyl chloride (1) (2 g, 10.1 mmol) and 3-aminotetrahydrofuran; (29)(1.0 ml, 11 mmol) in DCM (20 ml) and the solution stirred at room temperature for 4 hours. The solution was washed with 0.1N HCl (30 ml), saturated NaHCO$_3$ (30 ml), dried (Na$_2$SO$_4$), filtered and the solvents removed to give crude product which was further purified via crystallization from 15% EA in hexanes to give as a white solid.

Example 27

Methanone, (morphonyl) tricyclo[3.3.1.1$^{3,7}$]dec-1-yl-(Compound C1)

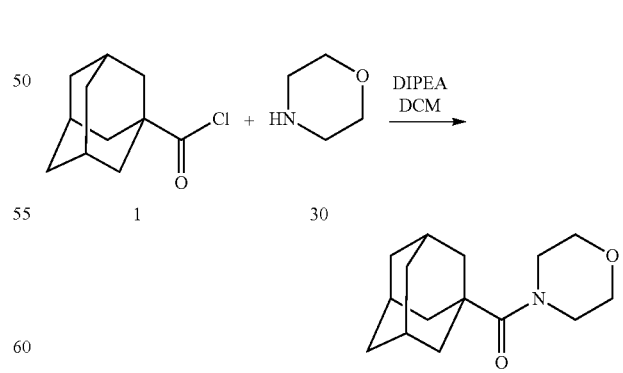

DIPEA (1.93 ml, 11.1 mmol) was added to a solution of Tricyclo[3.3.1.1$^{3,7}$]decane-1-carbonyl chloride (1) (2 g, 10.1 mmol) and morpholine; (30)(1.1 g) in DCM (20 ml) and the solution stirred at room temperature for 4 hours. The solution was washed with 0.1N HCl (30 ml), saturated NaHCO$_3$ (30 ml), dried (Na$_2$SO$_4$), filtered and the solvents removed to give crude product which was further purified via crystallization from 15% EA in hexanes to give as a white solid.

Example 28

Methanone, (piperidiny)tricyclo[3.3.1.1$^{3,7}$]dec-1-yl- (Compound C2)

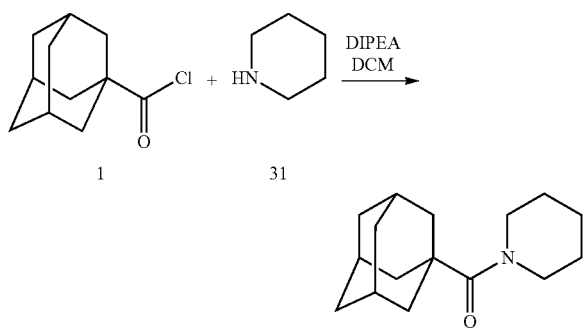

DIPEA (1.93 ml, 11.1 mmol) was added to a solution of Tricyclo[3.3.1.1$^{3,7}$]decane-1-carbonyl chloride (1) (2.1 g, 10.1 mmol) and piperidine (31) (1.1 g) in DCM (20 ml) and the solution stirred at room temperature for 4 hours. At this time, TLC 15:85 EA [ethylacetate: hexane, 20 µL aliquot into MTBE:1 N HCl (400 µL:400 µL)] showed the formation of a single product and some starting material. The solution was washed with 0.1N HCl (30 ml), saturated NaHCO$_3$ (30 ml), dried (Na$_2$SO$_4$), filtered and the solvents removed to give crude product which was further purified via crystallization from 15% EA in hexanes to give as a white solid.

Example 29

The following precursor cosmetic compositions were prepared and evaluated for crystals content, i.e. solubility of solid agent in the liquid agent.

Increased solubility of solid agent in the cosmetic precursor formulation of the invention may be visually confirmed by producing a precursor composition that includes solid agent, liquid agent and tricyclodecane amide, but is free of ingredients used solely to produce a cosmetic carrier or chassis such as water, polymeric thickeners, emulsifiers, sensory particles and pH modifiers or buffers. The composition is heated to a temperature above the melting point of the highest melting compound, then allowed to cool to room temperature. The precursor composition then was visually evaluated—generally, the precursor compositions of the invention were transparent or translucent, and remained so for at least 6 hours, preferably at least 12 hours, most preferably at least 24 hours. In the case of end use cosmetic compositions visualization of the crystals of solid agent was done by comparing a sample with and without tricyclodecane amide and observing the formation of crystals, if any, under the optical microscope fitted with cross-polarizers at a magnification of 10× or higher. The end use compositions of the invention contained substantially fewer crystals compared to compositions lacking tricyclodecane amides, and/or solid agent crystals that were still visible appeared to be much smaller in size. Decreased content/decreased size of the solid agent in the end use compositions of the invention allows the solid agent to be better dispersed in the compositions, allows for better delivery of the solid agent, and improved sensory feel of the composition.

The results that were obtained are summarized in Table 3. All observations for Table 3 were made using Leitz Labor-Lux Pol S optical microscope fitted with cross-polarizers at magnification of 40×.

OMC=Octylmethoxycinnamate
Pelemol GTIS=Triisostearin
Pelemol TISC=Triisostearyl citrate
PPG425=Polypropylene glycol
12-HSA=12-hydroxystearic acid
2-HEU=2-hydroxyethylurea
Glucam P-20=PPG-20 methyl glucose ether

TABLE 3

| Solid agent [S] (wt. %) | Liquid agent [L] (wt. %) | Ratio [S]/[L] | Tricyclodecane amide | straight chain comparator tetradecanoic acid (3 methyl-cyclohexyl)-amide | octadecanamide | phthalamide | Appearance after cooling - observation at 24 hours, except as noted | Outside the scope or within the scope of the invention |
|---|---|---|---|---|---|---|---|---|
| Avobenzone (28%) | OMC (40%) | 0.7 | Compound C21 (32%) | | | | Clear liquid | within |
| Avobenzone (41%) | OMC (59%) | 0.7 | | | | | crystals + liquid | outside (no tricyclodecaneamide) |
| Avobenzone (45%) | OMC (27.5%) | 1.6 | Compound C21 (27.5%) | | | | crystals + liquid | outside ([S]/[L] > 1/1) |
| Avobenzone (45%) | OMC (27.5%) | 2 | | X (27.5%) | | | crystals + liquid | outside (straight chain comparator) |
| Climbazole (28.5%) | Pelemol GTIS (42.8%) | 0.7 | Compounds* (C10, C14, C21) (28.5%) | | | | clear liquid | within |

TABLE 3-continued

| Solid agent [S] (wt. %) | Liquid agent [L] (wt. %) | Ratio [S]/[L] | Tricyclodecane amide | straight chain comparator tetradecanoic acid (3 methyl-cyclohexyl)-amide | octadecanamide | phthalamide | Appearance after cooling - observation at 24 hours, except as noted | Outside the scope or within the scope of the invention |
|---|---|---|---|---|---|---|---|---|
| Climbazole (10%) | Pelemol GTIS (90%) | 0.1 | | | | | crystal + liquid | outside (no tricyclodecaneamide) |
| Climbazole (50%) | Pelemol GTIS (25%) | 2 | Compound C14 (25%) | | | | crystal + liquid | outside ([S]/[L] > 1/1) |
| Cholesterol (16.6%) | OMC (50%) | 0.3 | Compounds* (C14, C10) (33.3%) | | | | Clear liquid | within |
| Cholesterol (16.6%) | OMC (50%) | 0.3 | Compound C21 (33.3%) | | | | Translucent gel | within |
| Cholesterol (16%) | OMC (84%) | 0.2 | | | | | crystal + liquid | outside (no tricyclodecaneamide) |
| Cholesterol (35%) | OMC (32%) | 1.1 | Compound C14 (33%) | | | | crystal + liquid | outside ([S]/[L] > 1/1) |
| Cholesterol (16.6%) | OMC (50%) | 0.3 | | | X (33.3%) | | crystal + liquid | outside (straight chain comparator) |
| Cholesterol (10%) | conjugated linoleic acid (45%) | 0.2 | Compound C14 (45%) | | | | clear liquid | within |
| Cholesterol (20%) | conjugated linoleic acid (80%) | 0.2 | | | | | crystals + liquid | outside (no tricyclodecaneamide) |
| Cholesterol (40%) | conjugated linoleic acid (30%) | 1.3 | Compound C14 (30%) | | | | crystals + liquid | outside ([S]/[L] > 1/1) |
| Climbazole (28.5%) | OMC (42.8%) | 0.7 | Compounds* (C10, C14, C21) (28.5%) | | | | clear liquid | within |
| Climbazole (30%) | OMC (70%) | 0.4 | | | | | crystal + liquid | outside (no tricyclodecaneamide) |
| Climbazole (55%) | OMC (22.5%) | 2.4 | Compound C14 (22.5%) | | | | crystal + liquid | outside ([S]/[L] > 1/1) |
| Climbazole (16.6%) | OMC (50%) | 0.7 | | | X (33.3%) | | crystal + liquid | outside (straight chain comparator) |
| Niacinamide (10%) | Glucam P-20 (55%) | 0.2 | Compounds* (C10, C14, C21) (35%) | | | | clear liquid | within |
| Niacinamide (10%) | Glucam P-20 (90%) | 0.1 | | | | | crystal + liquid | outside (no tricyclodecaneamide) |
| Niacinamide (35%) | Glucam P-20 (25%) | 1.4 | Compound C14 (40%) | | | | crystal + liquid | outside ([S]/[L] > 1/1) |
| Methyl Paraben (40%) | PPG-425 (40%) | 1 | Compound C14 (20%) | | | | clear liquid | within |
| Methyl Paraben (10%) | PPG-425 (90%) | 0.1 | | | | | crystal + liquid | outside (no tricyclodecaneamide) |
| Methyl Paraben (60%) | PPG-425 (25%) | 2 | Compound C14 (15%) | | | | crystal + liquid | outside ([S]/[L] > 1/1) |
| Salicylic acid (18%) | OMC (50%) | 0.4 | Compound C14 (32%) | | | | clear liquid | within |
| Salyclic acid (10%) | OMC (90%) | 0.1 | | | | | crystal + liquid | outside (no tricyclodecaneamide) |

TABLE 3-continued

|  |  |  |  | straight chain comparator | | | |  |
|---|---|---|---|---|---|---|---|---|
| Solid agent [S] (wt. %) | Liquid agent [L] (wt. %) | Ratio [S]/[L] | Tricyclodecane amide | tetradecanoic acid (3 methyl-cyclohexyl)-amide | octadecanamide | phthalamide | Appearance after cooling - observation at 24 hours, except as noted | Outside the scope or within the scope of the invention |
| Salicylic acid (60%) | OMC (25%) | 2.4 | Compound C14 (15%) |  |  |  | crystal + liquid | negative ([S]/[L] > 1/1) |
| 12HSA (16.6%) | OMC (50%) | 0.3 | Compounds* (C14, C10) (33%) |  |  |  | translucent gel | within |
| 12HSA (24.9%) | OMC (75.1%) | 0.3 |  |  |  |  | opaque solid | outside (no tricyclodecaneamide) |
| 12HSA (16.6%) | OMC (50%) | 0.3 |  | X (33%) |  |  | opaque solid | outside (straight chain comparator) |
| 12HSA (16.6%) | OMC (50%) | 0.3 |  |  |  | X (33%) | opaque solid | outside (phtalimide comparator) |
| 12HSA (16.6%) | Pelemol TISC (50%) | 0.3 | Compound C14 (33%) |  |  |  | translucent gel | within |
| 12HSA (24.9%) | Pelemol TISC (75.1%) | 0.3 |  |  |  |  | opaque solid | outside (no tricyclodecaneamide) |
| Climbazole (28.5%) | PPG425 (42.8%) | 0.7 | Compound C14 (28.5%) |  |  |  | clear liquid | within |
| Climbazole (40%) | PPG425 (60%) | 0.7 |  |  |  |  | crystals + liquid | outside (no tricyclodecaneamide) |
| Climbazole (45%) | PPG425 (35%) | 1.3 | Compound C14 (20%) |  |  |  | crystals + liquid | outside ([S]/[L] > 1/1) |
| 2-HEU (16.6%) | OMC (50%) | 0.3 | Compounds* (C10, C14) (33.3%) |  |  |  | clear liquid | within |
| 2-HEU (16.6%) | OMC (50%) | 0.3 | Compound C21 (33.3%) |  |  |  | Translucent gel | within |
| 2-HEU (24.9%) | OMC (75.1%) | 0.3 |  |  |  |  | crystal + liquid | outside (no tricyclodecaneamide) |
| 2-HEU (42%) | OMC (33%) | 1.3 | Compound C14 (25%) |  |  |  | crystal + liquid | outside ([S]/[L] > 1/1) |
| Cholesterol** (18%) | retinol proprionate (liquid at RT) (50%) | 0.4 | Compound C14 (32%) |  |  |  | clear liquid | within |
| Cholesterol** (20%) | retinol proprionate (liquid at RT) (80%) | 0.3 |  |  |  |  | opaque solid | outside (no tricyclodecaneamide) |
| Cholesterol** (18%) | retinol proprionate (liquid at RT) (50%) | 0.4 |  | X (32%) |  |  | opaque solid | outside (straight chain comparator) |
| Cholesterol** (45%) | retinol proprionate (liquid atr RT) (35%) | 1.3 | Compound C14 (20%) |  |  |  | opaque solid | outside ([S]/[L] > 1/1) |
| Salicylic acid (15%) | conjugated linoleic acid (35%) | .4 | Compound C14 (50%) |  |  |  | clear liquid | within |
| Salicylic acid (20%) | conjugated linoleic acid (80%) | .3 |  |  |  |  | opaque solid | outside (no tricyclodecaneamide) |

TABLE 3-continued

| | | | | straight chain comparator | | | | |
|---|---|---|---|---|---|---|---|---|
| Solid agent [S] (wt. %) | Liquid agent [L] (wt. %) | Ratio [S]/[L] | Tricyclodecane amide | tetradecanoic acid (3 methyl-cyclohexyl)-amide | octadecanamide | phthalamide | Appearance after cooling - observation at 24 hours, except as noted | Outside the scope or within the scope of the invention |
| Salicylic acid (42%) | conjugated linoleic acid (33%) | 1.3 | Compound C14 (25%) | | | | opaque solid | outside ([S]/[L] > 1/1) |
| Niacinamide** (9.1%) | PPG425 (54.5%) | 0.2 | Compounds* (C14, C10) (36.4%) | | | | clear liquid | within |
| Niacinamide** (14.5%) | PPG425 (85.5%) | 0.2 | | | | | opaque solid | outside (no tricyclodecaneamide) |
| Niacinamide** (35%) | PPG425 (32.5%) | 1.1 | Compound C14 (32.5%) | | | | opaque solid | outside ([S]/[L] > 1/1) |
| retinyl palmitate (28.5%) | OMC (42.8%) | 0.7 | Compound C14 (28.5%) | | | | clear liquid | within |
| retinyl palmitate (28.5%) | OMC (42.8%) | 0.7 | | | X (28.5%) | | crystal + liquid | outside (straight chain comparator) |
| Avobenzone (28.5%) | Propylene glycol (Log P~-1.3) (42.8%) | 0.7 | Compound C14 (28.5%) | | | | Crystal + liquid | outside (Log P liquid agent <-0.75) |

*experiments run separately with each of the tricyclodecane amides listed.
**observation at 12 hours.

Example 30

Example Using Hydrogel Based System

Figure 2:
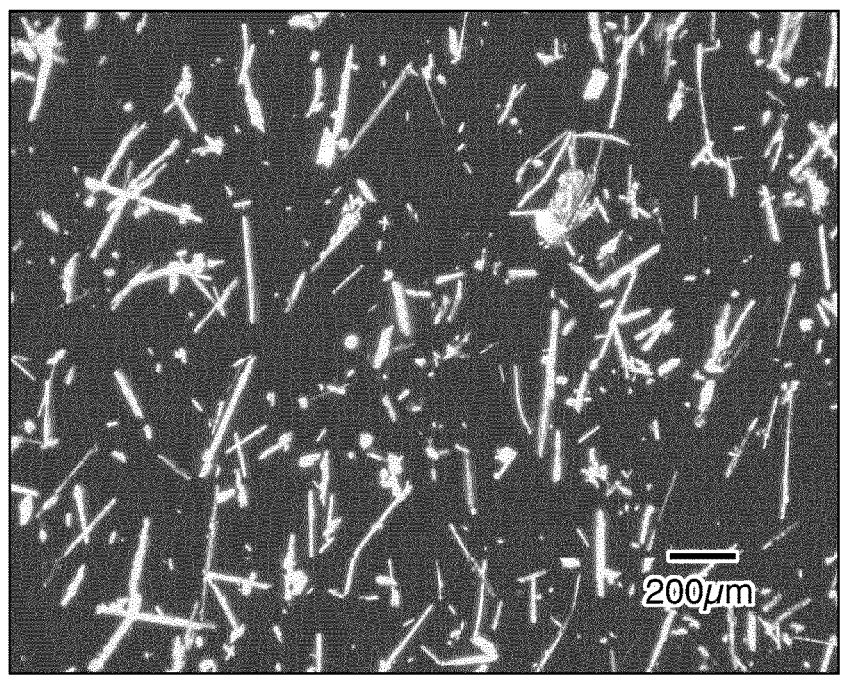

The following composition was made by first combining in the main tank, the Aristoflex AVC with water and mixing until homogeneous. The remaining ingredients were subsequently added to the main tank and mixed with heating to 85° C. The compositions were then cooled with mixing to room temperature to yield a cosmetic composition. Alternative methods could also be used such as combining water and water soluble ingredients, and oil and oil soluble ingredients. The two mixtures can then be heated to about 85° C. and subsequently combined and cooled to room temperature to yield a cosmetic composition. Still other processes known to those skilled in the art can also be used to prepare such a cosmetic composition which includes first preparing the precursor mixture following the procedure used in example 29. Separately the chassis components (polymeric thickener and water) are mixed until uniform gel is made. The two mixtures are then subsequently combined at room temperature with mixing to yield a cosmetic composition. In the case of the comparative example the composition was made by first combining in the main tank, the Aristoflex AVC with water and mixing until homogeneous. The remaining ingredients were subsequently added to the main tank and mixed with heating to 85° C. The compositions were then subsequently cooled with mixing to room temperature to yield a cosmetic composition. The composition that was prepared and the observations that were made are summarized in Table 4. Also see the microphotographs of the Sample 30 (FIG. 1) and Comparative Sample A (FIG. 2), made 72 hours after cooling to room temperature using Leitz Pol S optional microscope fitted with cross-polarizers at magnitude 40×.

TABLE 4

| | Sample 30 | Comparative Sample A |
|---|---|---|
| Polymeric thickener - Aristoflex AVC | 0.95% | 0.96% |
| Solid agent - Climbazole | 1.43% | 1.43% |
| Liquid agent - Pelemol GTIS | 2.14% | 2.14% |
| Tricyclodecane amide - Compound C14 | 1.43% | 0% |
| Water | q.s | q.s |
| Solid Agent/Liquid Agent Weight Ratio | 0.67 | 0.67 |
| Microscopic observation initially and at 2 weeks | Dramatically reduced amount of crystals and those that are present are smaller | presence of substantial amount of crystallized solid agent present as visibly large and long needle-like crystals |

Observation of both samples in a microscope fitted with cross-polarizers illustrates that the sample containing tricyclodecane amide has dramatically reduced amount of crystallized solid agent compared to the sample without tricyclodecane amide.

In the example above cosmetic carrier includes Aristoflex AVC and Water; and the cosmetic composition precursor is the mixture of the Climbazole, an ester—Pelemol GTIS, and Tricyclodecane amide.

Example 31

Example Using Oil-in-Water Emulsion

The following composition was made by first combining in the main tank, the Xanthan gum with water and mixing until homogeneous. The remaining ingredients were subsequently added to the main tank and mixed with heating to 85° C. The compositions were then cooled with mixing to room temperature to yield a cosmetic composition. Alternative methods could also be used such as combining water and water soluble ingredients, and oil and oil soluble ingredients. The two mixtures can then be heated to about 85° C. and subsequently combined and cooled to room temperature to yield a cosmetic composition. Still other processes known to those skilled in the art can also be used to prepare such a cosmetic composition which includes first preparing the precursor mixture following the procedure used in example 29. Separately the chassis components (polymeric thickener and water) are mixed until uniform gel is made. The two mixtures are then subsequently combined at room temperature with mixing to yield a cosmetic composition. In the case of the negative example the composition was made by first combining in the main tank, the Aristoflex AVC with water and mixing until homogeneous. The remaining ingredients were subsequently added to the main tank and mixed with heating to 85° C. The compositions were then subsequently cooled with mixing to room temperature to yield a cosmetic composition.

The composition that was prepared and the observations that were made are summarized in Table 5.

TABLE 5

| | Sample 31 | Comparative Sample B |
|---|---|---|
| Polymeric thickener - Xanthan gum | 0.47% | 0.47% |
| Emulsifier - Tween40 | 1.00% | 1.00% |
| Emulsifier - Span40 | 1.00% | 1.00% |
| Solid agent - Salicylic acid | 1.43% | 1.43% |
| Liquid agent - Octylmethoxycinnamate | 2.14% | 2.14% |
| Tricyclodecane amide - Compound C14 | 1.43% | 0% |
| Water | q.s | q.s |
| Solid Agent/Liquid Agent Weight Ratio | 0.67 | 0.67 |
| Microscopic observation initially and at 2 weeks | Free of crystallized solid agent | Presence of crystallized solid agent present as large needle-like crystals |

The following compositions in examples 32-35 were made by combining water and water soluble ingredients, and oil and oil soluble ingredients. The two mixtures were heated to about 85° C. to ensure all components were fully dissolved and subsequently combined and cooled to room temperature with mixing to yield a cosmetic composition. Alternative methods could also be used to those skilled in the art.

Example 32

Example Using Water-in-Silicone

The composition that was prepared and the observations that were made are summarized in Table 6.

TABLE 6

| | Sample 32 | Comparative Sample C |
|---|---|---|
| Silicone oil - DC 200 | 15% | 15% |
| Emulsifier - KSG310 | 5% | 5% |
| Solid agent - Avobenzone | 1.43% | 1.43% |

TABLE 6-continued

| | Sample 32 | Comparative Sample C |
|---|---|---|
| Liquid agent - Octylmethoxycinnamate | 2.14% | 2.14% |
| Tricyclodecane amide - Compound C14 | 1.43% | 0% |
| Water | q.s | q.s |
| Solid Agent/Liquid Agent Weight Ratio | 0.67 | 0.67 |
| Microscopic observation initially and at 2 weeks | Dramatically reduced amount of crystals | Presence of high concentration of crystallized solid agent |

Example 33

Example Using Conventional Skin Cream

The composition that was prepared and the observations that were made are summarized in Table 7.

TABLE 7

| | Sample 33 | Comparative Sample D |
|---|---|---|
| Polymeric thickener - Aristoflex AVC | 0.85% | 0.90% |
| Emulsifier - Cetyl alcohol | 0.40% | 0.40% |
| pH modifier - Triethanolamine | 0.79% | 0.79% |
| Emulsifier - Stearic acid | 2.48% | 2.48% |
| Emulsifier - Glyceryl Stearate | 0.69% | 0.69% |
| Solid agent - Salicylic acid | 2.18% | 2.18% |
| Liquid agent - conjugated linoleic acid | 3.57% | 3.57% |
| Tricyclodecane amide - Compound C14 | 5.00% | 0% |
| Water | q.s | q.s |
| Solid Agent/Liquid Agent Weight Ratio | 0.61 | 0.61 |
| Microscopic observation initially and at 2 weeks | Free of crystallized solid agent crystallized as needles and dramatically reduced amount of spherical type crystals | Presence of high concentration of crystallized solid agent present as both needles and spherical type crystals |

Example 34

Example Using Simulated Vanishing Cream

The composition that was prepared and the observations that were made are summarized in Table 8.

TABLE 8

| | Sample 34 | Comparative Sample E |
|---|---|---|
| Emulsifier - Fatty acid | 12.31% | 12.31% |
| Emulsifier - Fatty acid Soap | 3.20% | 3.20% |
| Solid agent - Avobenzone | 2.47% | 2.47% |
| Liquid agent - Octylmethoxycinnamate | 3.00% | 3.00% |

TABLE 8-continued

| | Sample 34 | Comparative Sample E |
|---|---|---|
| Tricyclodecane amide - Compound C14 | 4.00% | 0% |
| Water | q.s | q.s |
| Solid Agent/Liquid Agent Weight Ratio | 0.82 | 0.82 |
| Microscopic observation initially and at 2 weeks. | Dramatically reduced amount of crystallized solid agent present as large spherical type crystals, although both have large amount of crystals from other ingredients in the vanishing cream | Presence of high concentration of solid agent present as larger spherical type crystals |

Example 35

Example Using a Water-Oil Emulsion

The composition that was prepared and the observations that were made are summarized in Table 9.

TABLE 9

| | Sample 35 | Comparative Sample F |
|---|---|---|
| Liquid agent - Mineral oil | 15% | 15% |
| Emulsifier - KSG310 | 5% | 5% |
| Solid agent - Climbazole | 1.43% | 1.43% |
| Liquid agent - Pelemol ester GTIS | 2.14% | 2.14% |
| Tricyclodecane amide - Compound C14 | 1.43% | 0% |
| Water | q.s | q.s |
| Solid Agent/Liquid Agent Weight Ratio | 0.08 | 0.08 |
| Microscopic observation initially and at 2 weeks | Dramatically reduced amount of crystallized solid agent | High concentration of crystallized solid agent present as a distribution of both very large needles and small particles |

While described in terms of the presently preferred embodiments, it is to be understood that such disclosure is not to be interpreted as limiting. Various modifications and alterations will no doubt occur to one skilled in the art after having read the above disclosure. Accordingly, it is intended that the appended claims be interpreted as covering all such modifications and alterations as falling within the true spirit and scope of the invention.

The invention claimed is:

1. A cosmetic composition for topical application comprising:
   a) tricyclodecane amide:
   b) a solid agent; and
   c) a liquid agent
   d) wherein both the solid agent and the liquid agent is a cosmetic benefit agent; and
   e) wherein solid agent to liquid agent weight ratio is in the range from about 0.001 to about 1, wherein the tricyclodecane amide is selected from:

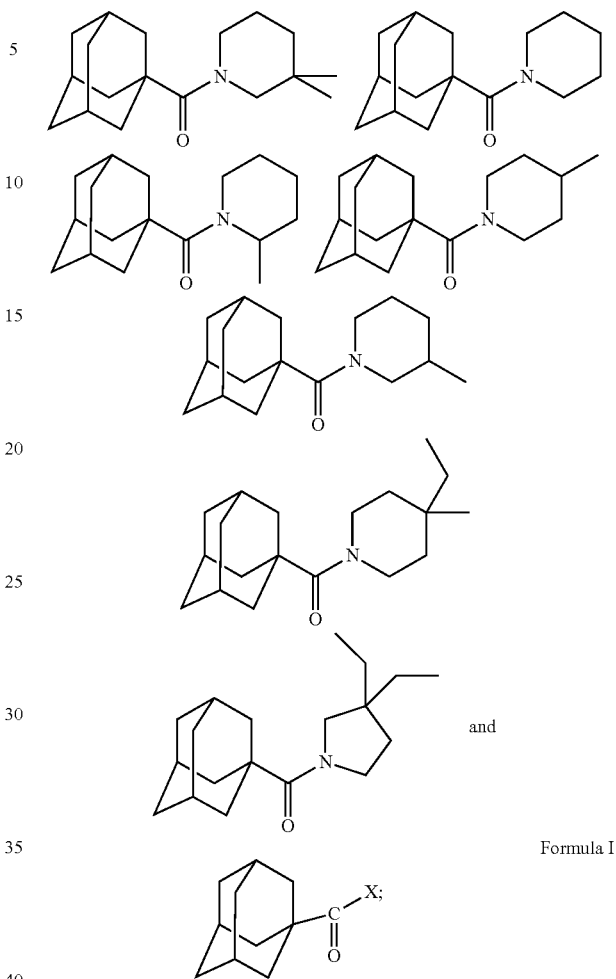

Formula I
where X is selected from:

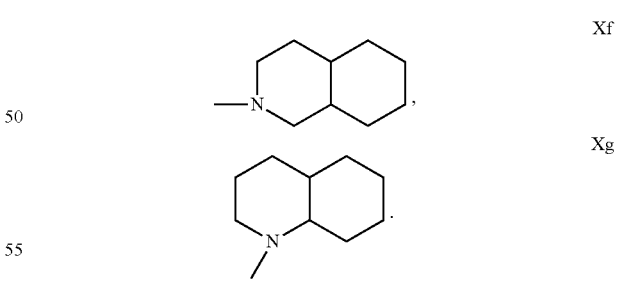

2. The composition according to claim 1, wherein the solid benefit agent in the composition is a sunscreen.

3. The composition according to claim 1, wherein the composition is a dentifrice, mouthwash, cream, lotion, balm, deodorant, gel, make-up composition, body wash, shampoo or conditioner.

4. The composition according to claim 1, wherein the solid agent to the liquid agent weight ratio is in the range from about 0.001 to 0.9.

5. The composition according to claim 1, wherein the solid benefit agent in the composition is selected from the group consisting of climbazole, ensulizole, butylmethoxy dibenzoylmethane, terephthalyidene dicamphor sulfonic acid, cholesterol, niacinamide, 12-hydroxystearic acid, glycolic acid, 2-hydroxyethyl urea, salicylic acid, polychloro phenoxy phenol, flavonoids like quercitin, petrolatum, retinyl palmitate, acetylglucosamine, undecylenoyl phenylalamine, dicarboxylic acids like octadecenedioic acid, C4-6 resorcinols, Vitamin D and its derivatives, dicaprylyl carbonate, caprylyl glycol, C1-6 parabens, and mixtures thereof.

6. The composition according to claim 1, wherein the solid benefit agent in the composition is a climbazole.

7. The composition according to claim 1, wherein the solid benefit agent in the composition is niacinamide.

8. The composition according to claim 1, wherein the solid benefit agent in the composition is a resorcinol.

9. The composition according to claim 8, wherein the resorcinol is selected from the group consisting of 4-butyl resorcinol, 4-ethyl resorcinol, 4-hexyl resorcinol, 4-phenylethyl resorcinol, dimethoxytoluyl propyl resorcinol, 4-cyclopentyl resorcinol, 4-cyclohexylresorcinol.

10. The composition according to claim 1, wherein the solid benefit agent in the composition is 12-hydroxystearic acid.

11. The composition according to claim 1, wherein the composition further comprises a preservative selected from the group consisting of iodopropynyl butyl carbamate, phenoxyethanol, imidazolidinyl urea, sodium dehydroacetate and benzyl alcohol.

12. The composition according to claim 1, wherein the liquid agent in the composition is selected from the group consisting of mineral oil, conjugated linoleic acid, petroselinic acid, isopropyl myristate, ethylhexyl salicyclate, caprylic/capric triglyceride, retinol propionate, octocrylene, methoxycrylene, octyl methoxycinnamate, PPG-20 methyl glucose ether, polypropylene glycol, and mixtures thereof.

13. A method of delivering a solid cosmetic agent topically to the skin of a consumer, comprising:
(a) obtaining the composition according to claim 1;
(b) applying the composition to the skin.

* * * * *